US007157620B2

(12) United States Patent
Connett-Porceddu et al.

(10) Patent No.: US 7,157,620 B2
(45) Date of Patent: **\*Jan. 2, 2007**

(54) ENHANCED TRANSFORMATION AND REGENERATION OF TRANSFORMED EMBRYOGENIC PINE TISSUE

(75) Inventors: Marie B. Connett-Porceddu, Summerville, SC (US); Heather J. Gladfelter, North Charleston, SC (US); Jon E. Gulledge, Goose Creek, SC (US); Ryan R. McCormack, Ithaca, NY (US)

(73) Assignee: Mead Westvaco Corporation, Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/973,088

(22) Filed: Oct. 10, 2001

(65) Prior Publication Data

US 2002/0100083 A1    Jul. 25, 2002

Related U.S. Application Data

(60) Provisional application No. 60/297,267, filed on Jun. 12, 2001, provisional application No. 60/239,143, filed on Oct. 10, 2000.

(51) Int. Cl.
*C12N 15/82* (2006.01)
*A01H 4/00* (2006.01)

(52) U.S. Cl. ............... 800/294; 800/278; 800/319; 800/268; 435/395; 435/469; 435/422; 435/430; 435/430.1; 435/431; 435/401

(58) Field of Classification Search ............... 800/294, 800/319, 278, 268; 435/469, 422, 430, 430.1, 435/395, 431, 401
See application file for complete search history.

(56) References Cited

U.S. PATENT DOCUMENTS

| 5,187,092 A | | 2/1993 | Uddin |
| 5,491,090 A | * | 2/1996 | Handley et al. ............ 435/422 |
| 5,856,191 A | * | 1/1999 | Handley, III ............... 435/422 |
| 6,200,809 B1 | | 3/2001 | Klimaszewska et al. |
| 6,340,594 B1 | | 1/2002 | Attree et al. |

OTHER PUBLICATIONS

Levee et al., Stable genetic transformation of white pine (Pinus strobus L.) after cocultivation of embrygenic tissues with Agrobacterium tumefaciens, 1990, Molecular Breeding, vol. 5, pp. 429-440.*
Levee et al (1999, Molecular Breeding 5(5):429-440).*
Levee et al (1999, Molecular Breeding 5:429-440).*
Pending U.S. Appl. No. 09/973,369, filed Oct. 9, 2001, by Connett-Porceddu et al.
Kong, Y. et al. (1988). "Culture of asparagus protoplasts on porous polypropylene membrane," *Plant Cell Reports* 7:67-69.
S.M. Attree et al., Somatic embryo maturation, germination, and soil establishment of plants of black and white spruce (*Picea mariana* and *Picea glauca*) Can. J. Bot 68:2583-2589 (1990).
T. Wei, "Genetic transformation of loblolly pine using mature zygotic embryo explants by *Agrobacterium tumefaciens*," Journal of Forestry Research 11(4):215-222, 2000.

* cited by examiner

*Primary Examiner*—Stuart F. Baum
(74) *Attorney, Agent, or Firm*—Rothwell, Figg, Ernst & Manbeck

(57) ABSTRACT

The present invention relates to methods for the transformation and regeneration of transformed embryogenic tissue of coniferous plants. In particular, the invention relates to improved methods for transforming embryogenic tissue of coniferous plants and for regenerating transformed embryogenic tissue of coniferous plants. The invention is well suited to the transformation and regeneration of transformed embryogenic tissue of plants of the subgenus *Pinus* of pines and hybrids thereof.

75 Claims, No Drawings

ENHANCED TRANSFORMATION AND REGENERATION OF TRANSFORMED EMBRYOGENIC PINE TISSUE

The present application is related to U.S. provisional patent application Ser. No. 60/297,267 filed on 12 Jun. 2001 and to U.S. provisional patent application Ser. No. 60/239,143 filed on 10 Oct. 2000, each incorporated herein by reference, and priority thereto is claimed under 35 USC §119(e).

BACKGROUND OF THE INVENTION

The present invention relates to methods for the transformation and regeneration of transformed embryogenic tissue of coniferous plants. In particular, the invention relates to improved methods for transforming embryogenic tissue of coniferous plants and for regenerating transformed embryogenic tissue of coniferous plants. The invention is well suited to the transformation and regeneration of transformed embryogenic tissue of plants of the subgenus *Pinus* of pines.

The publications and other materials used herein to illuminate the background of the invention or provide additional details respecting the practice, are incorporated by reference, and for convenience are respectively grouped in the appended Bibliography.

Reforestation, the controlled regeneration of forests, has become an integral part of forest management in order to secure a renewable and sustainable source of raw material for production of paper and other wood-related products. Forest trees can be regenerated by either sexual or asexual propagation. Sexual propagation of seedlings for reforestation has traditionally been the most important means of propagation, especially with coniferous species.

Tree improvement programs with economically important conifers (e.g., *Pinus, Picea,* and *Pseudotsuga* species) have applied genetic principles of selection and breeding to achieve genetic gain. Based on the results of progeny tests, superior maternal trees are selected and used in "seed orchards" for mass production of genetically improved seed. The genetic gain in such an open-pollinated sexual propagation strategy is, however, limited by the breeder's inability to control the paternal parent. Further gains can be achieved by control-pollination of the maternal tree with pollen from individual trees whose progeny have also demonstrated superior growth characteristics. Yet sexual propagation results in a "family" of seeds comprised of many different genetic combinations (known as siblings), even though both parents of each sibling seed are the same. As not all genotype combinations are favorable, the potential genetic gain is reduced due to this genetic variation among sibling seeds.

In addition to these genetic limitations, large-scale production of control pollinated seeds is expensive. These economic and biological limitations on large-scale seed production have caused considerable interest to develop in the industry for applying asexual methods to propagate economically important conifers.

The use of asexual propagation permits one to apply what is known as a very high selection intensity (that is, to propagate only progeny showing a very high genetic gain potential). These highly desirable progeny have unique genetic combinations that result in superior growth and performance characteristics. Thus, with asexual propagation it is possible to multiply genetically select individuals while avoiding a concomitant reduction of genetic gain due to within-family variation. Asexual propagation of trees can be accomplished by methods of grafting, vegetative propagation, and micropropagation. Micropropagation by somatic embryogenesis refers to methods whereby embryos are produced in vitro from small pieces of plant tissue or individual cells. The embryos are referred to as somatic because they are derived from the somatic (vegetative) tissue, rather than from the sexual process. Both vegetative propagation and micropropagation have the potential to capture all genetic gain of highly desirable genotypes. However, unlike conventional vegetative propagation methods, somatic embryogenesis is amenable to automation and mechanization, making it highly desirable for large-scale production of planting stock for reforestation. In addition, somatic embryogenic cultures can easily be preserved in liquid nitrogen. Having a long-term cryogenic preservation system offers immense advantages over other vegetative propagation systems which attempt to maintain the juvenility of stock plants.

One source of new genetic material for use in reforestation or tree improvement programs is plant tissue that has been transformed to contain one or more genes of interest. Genetic modification techniques enable one to insert exogenous nucleotide sequences into an organism's genome. A number of methods have been described for the genetic modification of plants, including transformation via biolistics and *Agrobacterium tumefaciens*. All of these methods are based on introducing a foreign DNA into the plant cell, isolation of those cells containing the foreign DNA integrated into the genome, followed by subsequent regeneration of a whole plant.

A significant problem in production of transgenic plants is how to recover only transformed cells following transformation, while causing minimal perturbations to their health so that they can proliferate, give rise to differentiating cultures and ultimately regenerate transgenic plants.

It is well known that embryogenic cultures, in general, and pine embryogenic cultures, specifically, can experience significant decline in regeneration potential under stressful culture conditions. Stresses to the cells during and after transformation can include the perturbations of the transformation process (which may include co-cultivation with *Agrobacteria,* bombardment with microprojectiles, chemical treatments, electroporation or mechanical shearing), any measures that allow preferential growth of transformed cells while selectively killing or depressing the growth or regeneration of untransformed cells (referred to as "selection"), exudates released from dying cells in the culture, and/or the elicitation of transgene activity in the transformed cells (for "positive selection" or detection of the activity of "visual marker genes"). It stands to reason that when transformed cells are not maintained in sufficient health to allow their survival through these stresses, not only will they fail to give rise to transgenic plants, they may never be detected as transformed in the first place.

In a plant genetic transformation process using *Agrobacterium tumefaciens* as the transforming agent, a usual step is to place the infected plant tissue, after a suitable "co-cultivation period", into a liquid medium or onto the surface of a gelled medium which incorporates an eradicant for the *Agrobacterium*. This is done to kill the *Agrobacterium*, which, after it has accomplished gene transfer into the plant, is a hazard to sterile culture and subsequent good growth of the plant material. Eradication usually involves multiple transfers of the plant cells into uncontaminated media containing antibiotics such as ticarcillin, carbenicillin, or a cephalosporin. The antibiotics are normally incorporated into every stage of the medium following transformation, to prevent *Agrobacterium* contamination from resurging.

Regeneration of transformed plants from transformed cultures of pine has been difficult. Reports of pine transformation and regeneration include the following:

U.S. Pat. No. 4,459,355 (Cello and Olsen, 1984) describes a method for using *Agrobacterium tumefaciens* to transform plant cells. The patent claims transformation of any dicotyledon or any gymnosperm (e.g. loblolly pine, cedar, Douglas fir). However, no example of transformation of any gymnosperm is given. Thus, a claim of stable transformation of pines following inoculation with *Agrobacterium tumefaciens* was allowed in U.S. Pat. No. 4,886,937 (Sederoff et al., 1989).

U.S. Pat. No. 4,886,937 also claims the transformed pine obtained from inoculation with *Agrobacterium tumefaciens*. However, no transformed pine plants were obtained in the examples, which are restricted to formation of non-regenerable galls following inoculation of seedlings. Further work by researchers in the same lab, using *Agrobacterium tumefaciens* to inoculate pine and spruce somatic embryogenic cultures, was published (Wenck et al., 1999). In the work described in this publication, stable transformation of both species was achieved, but while plants were regenerated from the transformed spruce cultures, no plants could be obtained from the loblolly pine cultures.

U.S. Pat. No. 5,565,347 (Fillatti and Thomas, 1996) claims transformation of plants by co-cultivation of cotyledon shoot cultures with *Agrobacterium*, but again no example of transformation of any gymnosperm is given. Recovery of plants transformed via *Agrobacterium* from species of the subgenus *Pinus* via methods similar to those claimed in U.S. Pat. No. 5,565,347 has not been achieved with high frequency. There is a report of stable transformation of *Pinus taeda* specifically by inoculating shoot apices using the methods of U.S. Pat. No. 5,164,310 (Smith et al., 1992; which claimed the application of these methods to flowering plants, not conifers), but regeneration of transformed plants was a very low frequency occurrence. Stable transformation of *Pinus radiata* by inoculating cotyledons and later lateral buds has been reported publicly (Connett et al. 1993), but again regeneration of transformed plants was a very low frequency occurrence. Methods using shoot apices, lateral buds, cotyledons and similar tissue have a high probability of regenerating chimaeric plants. This, combined with the low frequency of regeneration, results in such methods being considered inviable for large-scale production of transformed plants.

Transformation of embryogenic cultures of gymnosperms has been a means of producing largely non-chimaeric transformed plants. Most reports of transformation of embryogenic cultures of gymnosperms, and all reports which featured regeneration of plants suitable for field planting from embryogenic cultures of pines of the subgenus *Pinus*, use biolistic transformation methods. However, those skilled in the art recognize that biolistic transformation methods have disadvantages relative to *Agrobacterium*-mediated transformation, such as the delivery of relatively smaller pieces of heterologous DNA in relatively higher copy numbers, with relatively more rearrangements seen on incorporation into the plant chromosomes.

Stable transformation of embryogenic cultures of *Pinus strobus* by *Agrobacterium*, followed by regeneration of plants, has been presented in a public forum (Séguin et al. 1999, IUFRO Wood Biotechnology conference). *Pinus strobus* is in the subgenus *Strobus*, or soft pines, while the Southern yellow pines such as *Pinus taeda, Pinus elliotii,* and *Pinus caribaea*, as well as the Eastern hard pines such as *P. rigida, P. serotina, P. nigra* and *P. sylvestris*, and the Western hard pines such as *P. radiata* and *P. attenuata* are in the subgenus *Pinus*. It is well known to those skilled in the art that the somatic embryogenesis systems for soft pines are different from those of the genetically different hard pines. Regeneration of plants following stable transformation of embryogenic cultures of any pine of the subgenus *Pinus* by *Agrobacterium* has not been reported in the literature.

A second problem, particularly relating to *Agrobacterium* transformation, has to do with the means of eradication of *Agrobacterium* following co-cultivation. Methods that have been employed in *Agrobacterium* transformation by those skilled in the art comprise physical washing of the bacteria from the plant cells and application of eradicants such as antibiotics in the plant culture media. Washing procedures are considered by those skilled in the art to be disadvantageous because they can result in significant loss of potentially transformed plant cells and damage to those that remain due to anaerobicity in the wash liquid, incomplete transfer, and shearing during movement of the cells from one medium to another. On the other hand certain eradicants, commonly used by those skilled in the art of transformation in order to kill the *Agrobacterium*, when incorporated into wash media or into media used for post-transformation recovery, selection, and/or proliferative growth, are detrimental to the subsequent differentiation of pine embryos that could give rise to transformed pine plants. In addition, eradicants incorporated into embryo development and maturation media are sometimes rendered partially or wholly inactive due to the high temperature of polymerization of the media. Moreover, the continuous incorporation of these eradicants in culture media is relatively expensive.

A third problem, relevant to any transformation method useful for groups of smaller, less differentiated cells such as precotyledonary somatic embryos, cell suspensions, or clumps of callus, is the detrimental nature of practices commonly used for post-transformation selection of transformed cells, which include laying the cells on filter papers or directly on the surface of gelled media. Detrimental conditions that can develop at the interfaces, such as anaerobicity, accumulation of exudates from necrotic cells, and barriers to diffusion of selection agents, nutrients, and plant growth regulators, are often exacerbated by incomplete transfer of cells from one medium to another, or transfer of cells with bits of spent media clinging to the desired material that also form a barrier to diffusion.

Thus, it is an object of the present invention to provide improved methods for the transformation of coniferous plants and the regeneration of transformed coniferous plants. These methods include improved methods for minimizing physical damage to cells during transformation and subsequent steps, for eradicating *Agrobacterium* from cell culture, for selecting genetically transformed pine cells, for growing pine cell cultures on "double layer" or "biphasic" culture systems, for transferring pine cell cultures between liquid and gelled media, gelled and liquid media, different liquid media or different gelled media, and for enhancing efficiency of regeneration with the use of certain components in the media.

SUMMARY OF THE INVENTION

The present invention relates to methods for the transformation of embryogenic tissue of coniferous plants and the regeneration of transformed embryogenic tissue of coniferous plants. The invention is well suited to the transformation and regeneration of transformed embryogenic tissue of plants of the subgenus *Pinus* of pines. The present invention provides for the first time the regeneration of plants suitable for field planting from *Agrobacterium*-transformed lines of the subgenus *Pinus* of pines.

There are many parameters involved in the transformation and regeneration of plants. Prior to the present invention, the necessary parameters leading to successful regeneration of transformed plants of the hard pines, particularly the Southern yellow pines and hybrids thereof, from *Agrobacterium*-transformed somatic embryogenic cultures had not been discovered. Although hard pines could be regenerated through embryogenesis, a successful method for the regeneration of plants suitable for field planting from *Agrobacterium*-transformed embryogenic hard pine tissue had not been performed. The present invention is the first instance of the regeneration of *Agrobacterium*-transformed embryogenic tissue of the hard pines. Such regeneration is possible by improvements in several parameters in the overall transformation and regeneration techniques. These parameters include (a) minimizing physical damage to cells during transformation and subsequent steps, (b) selecting genetically transformed pine cells, (c) eradicating *Agrobacterium* from the pine cell culture, (d) where appropriate, growing pine cell cultures on "double layer" or "biphasic" culture systems and (e) where appropriate, transferring pine cell cultures between liquid and gelled media, gelled and liquid media, different liquid media or different gelled media. There is often an interrelationship between these parameters, such that an improvement with respect to one parameter will be useful for a second parameter and may constitute part of an improvement with respect to that second parameter.

Physical damage to cells during transformation and subsequent steps is minimized by several means. A washing procedure is used wherein significant improvement in the recovery of pine cells was made by minimizing and any crushing of the cells for resuspension, by use of wide-mouthed, aerated vessels for immersion in liquid media and support membranes for the plating of pine embryogenic cells before and after *Agrobacterium*-mediated transformation and each washing episode. The support membranes allowed the liquid media to be removed from the cells by vacuum filtration, with minimal loss of cells and minimal carryover of contaminated medium.

The transfer of pine material between liquid and gelled media such as the wash media in the step described above, or between different gelled media, facilitated by the use of nylon or cellulosic-based supports as previously taught in the literature, can be improved using a support made of non-swelling fibers, such as a polyester or fluoropolymer membrane, through which media components may penetrate more readily, and to which the pine material does not cling as readily as it does to cellulosic-based supports or fabric supports made of fibers such as nylon that swell appreciably when in contact with liquid.

A further improvement is observed by a method for eradicating from cell culture any *Agrobacterium* contamination surviving the improved wash method described above, by use of an overlay in which the eradicants are incorporated in a medium to be overlaid on a gelled medium, most preferably a liquid medium that is similar to the gelled medium except for the absence of gelling agents and the presence of the eradicant(s). This method abolishes the need for the continuous use of eradicants, which we have found often to be detrimental to the pine cell cultures, in the gelled media throughout most of the culture period following transformation. It was found that, the culture of cells over a bilayer formed by liquid medium pipetted in a thin film over gelled maintenance media, or saturated into a filter paper "sponge" laid on gelled maintenance media, is not as detrimental to the growth and subsequent embryogenicity of cells as is the culture of cells over gelled media containing eradicants. The growth and development of pine cell cultures on culture media, particularly selection and eradication media such as the eradication system described above which can be viewed as a "double layer" or "biphasic" culture system comprised of two gelled phases or a gelled phase overlaid with liquid medium, can be improved via the method of employing a thin non-cellulosic based support made of non-swelling, acid-resistant fibers, such as a polyester or fluoropolymer membrane, easily penetrable by plant growth factors and other large molecules, supporting the pine tissue. The use of a thin non-cellulosic based support made of non-swelling, acid-resistant fibers, such as a polyester or fluoropolymer membrane, over culture media, particularly "double layer" or "biphasic" culture systems comprised of two gelled phases or a gelled phase overlaid with liquid medium, also facilitates rapid and complete culture transfers. This is particularly important during the eradication processes that follow *Agrobacterium* transformation, because the use of a support on which the cells can be rinsed and to which gelled medium does not cling minimizes both carryover of the smaller bacterial cells and compounds released into the medium by necrotic cells, and does not create barriers to diffusion into the pine cells of antibiotics from the replacement medium.

Selection of genetically transformed pine cells is improved by several means.

With the use of these means, selection of transformed lines is accomplished more rapidly, as well as increasing the health of the cells going into the embryo development phase and decreasing the time prior to differentiation of embryos. One measure facilitating this was the use of permeable support membranes, preferably polyester or fluoropolymer membranes, most preferably polyester support membranes, rather than laying the cells on filter papers or directly on the surface of gelled media. The cells, once plated onto the support, could be very easily transferred from the surface of one gelled medium to another with minimal damage, and minimal carryover of paper fragments or spent media that could contain exudates from necrotic cells. Also, more even dispersal of cells on the surface of the support membrane was possible than on filter papers or semi-solid media. A thin layer of culture tissue, rather than thick layers or clumps, increases the likelihood that most or all cells will be exposed to the selective agents, and speeds the selection process.

DETAILED DESCRIPTION

Several improvements, taken together, allow the regeneration of transformed embryos of hard pines, i.e. pines of the subgenus *Pinus*, particularly Southern yellow pines and hybrids thereof. Examples of Southern Yellow pines include *Pinus taeda, Pinus elliotii*, and *Pinus caribaea*. Other hard pines to which the method is suited include *Pinus radiata, P. palustris, P. sylvestris*, and *P. rigida*. Other hard pines include *P. serotina, P. patula, P. nigra* and *P. attenuata*.

The first improvement is the minimization of the physical damage that occurs to cells during the transformation and washing processes. Several means are used to accomplish this minimization of physical damage.

A) While an initial step in eradication of *Agrobacterium*-transformed cells can be a series of physical washes, the total duration of washes and the number of manipulations used are minimized. This is valuable not only because fewer pine cells are lost during the washing process, but because it has been found that washes of shorter total duration and greater aerobicity can improve recovery time, i.e., the time to regain pre-transformation growth rates. In this invention we are able to substantially reduce or eliminate *Agrobacterium* contamination of the pine cells using washes individually lasting from minutes to overnight for a total duration of less than two days, whereas previous work found that total eradication of *Agrobacterium* contamination in the pine cells was accomplished only after four or more days of washes. This improvement is due, in part, to the use of support membranes discussed further below.

B) Vessels are used for the wash process such that damage to the cells going in and out of the washes is minimized without compromising either the physical contact of pine cells with the wash media (which is responsible for the eradication of bacterial cells), or the air-media interface area and thus aerobicity of the cultures during the wash period. An improvement over vessels commonly used for washing procedures, such as flasks, wherein the cells can be crushed or lost in the cumbersome process of passing into such wash containers, consists of using wide-mouthed jars, most preferably with aerated lids that maintain axenic conditions while providing aeration to the pine cells. An example of such vessels comprises "baby food" jars with MAGENTA® aerated lids (available from SIGMA), most preferably in a size such that they can be fixed with standard clamps similarly to flasks for agitation on automatic shakers, providing further aeration of the pine cells and maximizing physical contact of the pine cells with the wash media.

C) In washing procedures the cells are transferred from the medium in or on which they were inoculated into wash medium, then (possibly repeatedly) transferred by resuspension into fresh aliquots of this liquid medium. Incomplete transfer of cells from the semi-solid medium surface (which often results in loss of many of the possibly transformed cells) is greatly reduced through the use of polyester or fluoropolymer supports. We found employment of polyester or fluoropolymer supports for the collection and plating of pine embryogenic cells before and after *Agrobacterium*-mediated transformation, and before and after each washing episode, to be beneficial during the washing procedures because the support membranes allow the liquid media to be removed from the cells by vacuum filtration, with minimal loss of cells and minimal carryover of contaminated medium (such carryover was further minimized by gentle rinsing of the cells supported on the membranes, with removal of rinse media by vacuum filtration) and because supports made of such non-swelling materials, unlike filter papers or nylon supports, released the cells easily into the wash vessels, thus averting any crushing of the cells for resuspension and speeding both resuspension and replating of the embryogenic cells, decreasing the total duration in unagitated (anaerobic) liquid during any single washing step. Moreover, because the resuspension and replating of the cells is much faster, and more efficient, fewer wash steps of shorter duration are able to eradicate the *Agrobacterium*, resulting in less collateral damage to transformed pine cells. Experiments were conducted wherein *Agrobacterium*-infected pine embryogenic cells, which had been washed by our improved method employing polyester or fluoropolymer supports, were replated onto medium that did not contain antibiotics. No significant contamination of the replated pine cells by the *Agrobacterium* was observed in these experiments. The experiments were repeated with two different strains of *Agrobacterium*, including a hypervirulent strain.

The support membranes further allowed the placement of the washed and rinsed cells, with little physical manipulation required, on uncontaminated gelled media for subsequent culture and selection.

The second improvement involves continuing culture of the pine cells, following transformation and washing, on non-cellulosic based support membranes placed over gelled nutrient media, as an alternative to maintaining, developing, maturing, or regenerating pine cultures on the surface of the gelled media (wherein the cells tend to become partially embedded) or on filter papers or cellulosic pads (which can adsorb components of the media). We have found that constituents of tissue culture media (such as plant growth regulators, selection agents, antibiotics and the like) readily pass through non-cellulosic based support membranes such as polyester, polypropylene, liquid permeable fluoropolymers (e.g., ethylene tetrafluoroethylene (ETFE) and the like. We have also found that a growth and regenerability advantage was conferred with the use of such supports, perhaps due to decreased formation of necrotic regions (which commonly appeared in cultures maintained on gelled or biphasic media without such support membranes, in the wet and anaerobic spaces directly adjacent to the surface of the medium). Moreover, the use of such support membranes permits the tissue cultured callus or cells to be spread thinly over the surface of membranes, also preventing tissue from becoming partially embedded in the media (and consequently becoming anareobic), while still enabling the media components, such as antibiotics for selection, to reach the cultures more effectively over the entire surface via capillary action.

In this improvement, the target pine cells are cultured following transformation on polyester or fluoropolymer support membranes placed over gelled support media containing a selection agent. Experiments were conducted to determine whether selection agents (such as kanamycin, GENETICIN® antibiotic, herbicides, and the like) would be able to pass from the underlying medium through non-cellulosic support membranes to tissue in contact with the membrane. Our results indicate that the selection agents kanamycin, GENETICIN® antibiotic and various herbicides of interest were able to pass through polyester support membranes, selecting tissue which has been transformed with a kanamycin, GENETICIN® antibiotic or herbicide resistance gene by killing tissue which has not been transformed with this gene. Indeed, the incidence of "escapes" (i.e., untransformed cells which fail to be killed by the selection agent) was found to be lower when polyester support membranes were employed in the selection method than when the cells are cultured directly on the surface of media containing the selection agent, or when filter paper or nylon supports were used.

Experiments with organic dyes demonstrated that passage through polyester membranes from the underlying medium into the tissue above the membrane is faster than through nylon membranes. Thus the improved results obtained via use of the present selection method may in part be due to an improved flow of selection agent through the polyester support membrane. Unlike nylon or cellulose, polyester fibers do not swell appreciably when wetted, regardless of mesh size and weave type. The improved results obtained via use of the present selection method may also be due in part to a decrease in the appearance of necrotic clumps of cells directly adjacent to the medium (which allows the selection agent to reach more of the growing cells unimpeded). The effect is particularly pronounced when the support membranes are made of a fiber or material that does not swell appreciably as a result of taking up and retaining liquid from the medium or fray in contact with the acidic pH common to plant media, such as polyester, ETFE or polypropylene. Specifically, experiments have shown the growth rate and regenerability of pine cells on polyester or ETFE support membranes over gelled media to be either equal to, or superior to, the growth rate of cultures maintained directly on the gelled media or on nylon membranes. Thus, the second improvement allows the selection of transformed lines more rapidly and with increased health of cells going into the embryo development phase. This improvement results in a decrease in the time prior to the differentiation of embryos.

While a variety of support membranes can be employed in the improved method for selectively growing transformed pine cells during the selection and eradication processes and thereafter, it is preferred to use polyester or liquid-permeable fluoropolymer support membranes due to lack of retention of liquid media within the fibers, and resistance to the mildly acidic conditions that often prevail in plant tissue cultures. A range of mesh sizes has been tested and found satisfactory for growth of pine cells; and it is believed that pore sizes ranging from a few microns (to allow permeability to liquid medium and complex organic molecules) up to about half the size of the cells being cultured (to avert loss of the cultured cells through the mesh) can be used. As noted above, it is often quite difficult to remove cells completely where nylon membrane solid supports are employed, as the cells often tend to adhere among the swollen nylon fibers (which also result in a greatly decreased effective mesh size in the wetted membranes). The decreased effective mesh size can result in poor penetration of large molecules, and the adherence of cell culture material among the swollen fibers can necessitate a significant amount of agitation and scraping to remove the cells from the solid supports—actions which potentially damage many of the cells that are being transferred. It can also be difficult to remove tissue completely from filter papers or thick fibrous pads such as polyester, nylon or cellulosic "batting", "felting" or "sponges" because the tissue becomes entwined in the surface fibers. This problem is exacerbated when the material becomes frayed in contact with the wet, acidic plant culture media. Thus, the use of smooth polyester or liquid-permeable fluoropolymer support membranes is preferred over nylon or over thick fibrous or felted pads because the use averts both the cell adherence problem and the lack of penetration by macromolecules such as plant growth regulators, polymers, selection agents, eradicants, and the like.

Furthermore, it is easier to disperse the callus or tissue more evenly on the surface of the support membrane using the improved method than it is to disperse the cells without partially embedding them on gelled media. The ability to grow the cells at lower densities on selection and/or to utilize a thin layer of culture tissue, rather than the relatively thick layers or clumps associated with the use of traditional selection methods, increases the likelihood that most or all cells will be exposed to the selective agents.

Furthermore, resuspension of callus-type or embryogenic cells in controlled volumes, for example in order to replate at lower density for increasing selection pressure, is also facilitated because the cells are easily dispersed from the polyester fabric into liquid media, and easily captured on polyester membranes over a Buchner funnel for replacement onto fresh gelled media.

Thus, the support membrane may be used for transferring a liquid suspension plant tissue culture to a gelled medium or to a fresh liquid medium or to facilitate the transfer of cells from one gelled medium to another. The use of a thin non-cellulosic based support made of non-swelling, acid-resistant fibers, such as a polyester or fluoropolymer membrane, over culture media, facilitates rapid and complete culture transfers. Fewer cells are lost or damaged when polyester or fluoropolymer support membranes are employed, thereby allowing a greater recovery of viable cells.

The third improvement is the use of double layer, bilayer or biphasic culture systems for selection of the transformants and eradication of the *Agrobacterium*. It was found that the culture of cells over a bilayer formed by liquid medium pipetted in a thin film over gelled maintenance media, or saturated into a filter paper "sponge" laid on gelled maintenance media, is not as detrimental to the growth and subsequent embryogenicity of cells as is the culture of cells over gelled media containing eradicants. The growth and development of pine cell cultures on culture media such as these can be viewed as a "double layer" or "biphasic" culture system comprised of two gelled phases or a gelled phase overlaid with liquid medium. Such a system can be improved via the method of employing a thin non-cellulosic based support for the pine tissue, made of non-swelling, acid-resistant fibers such as polyester or fluoropolymer, easily penetrable by large molecules such as antibiotics. As mentioned above, experiments with organic dyes have shown that relatively large molecules are able to pass through polyester support membranes (but not as rapidly through nylon support membranes) from underlying media into cells cultured on the membranes. For molecules used in selection of pine transformants or eradication of *Agrobacterium* from transformed pine tissue cultures (such as antibiotics or positive selection agents), heat lability, slow diffusion through gelled media, or other osmotic effects may limit the efficacy if they are incorporated into gelled media. Accordingly, a preferred improved selection and/or *Agrobacterium* eradication method (a "support membrane bi-layer" system) for pine cell culture comprises the application of antibiotics in a thin film of liquid medium on top of the gelled support medium under the polyester or liquid-permeable fluoropolymer support membrane, or in liquid absorbed in a layer of filter paper between the gelled medium and the support membrane, thereby allowing the antibiotics to pass through the support membrane into the cultured cells. The liquid medium used to incorporate the compounds of interest in this improved method is similar in composition to the gelled medium on which the pine tissue is grown, except that the gelling agents and any adsorbing components (such as activated charcoal) may be omitted, and antibiotics or other selection or eradication components may be added.

An added benefit of this improved culture method using support membranes over the gelled and liquid phases is that selection and/or antibiotic treatment for eradication of *Agrobacterium* can be resumed or continued through all phases of embryo growth and development if necessary, because it can be employed with any tissue culture phase or step that does not involve the formation of roots into the culture medium. For example, the tissue culture method can be employed with a selection and/or eradication medium based on a maintenance medium, a proliferation medium, an embryo development medium, a maturation medium, or a regeneration medium.

Accordingly, a preferred improved method (a "bi-layer" system) for selection of transformed cells comprises the application of selective agents in a thin film of liquid medium on top of the gelled support medium under the polyester or liquid-permeable fluoropolymer support membrane, or in liquid absorbed in a layer of filter paper between the gelled medium and the polyester support membrane, thereby allowing the molecules of interest to pass readily through the support membrane into the cultured pine cells. Selection agents can be heat-labile at the temperatures required for polymerization of gelled media. Thus, an additional advantage to this method is that the selection agents, added in liquid media that can be filter-sterilized, are not subjected to the temperatures used to sterilize and polymerize gelled media. The liquid medium used to incorporate the compounds of interest in this improved method is similar in composition to the gelled medium on which the pine tissue is grown, except that the gelling agents and any adsorbing components (such as activated charcoal) are omitted, and selection agents may be added. This improved method of selecting transformed pine, using support membranes, can be employed with any tissue culture phase or step that does not involve the formation of roots into the culture medium. For example, the tissue culture method can be employed with a selection and/or eradication medium based on a maintenance medium, a proliferation medium, an embryo development medium, a maturation medium, or a regeneration medium.

Furthermore, a preferred improved method (a "bi-layer" system) for eradicating *Agrobacterium* from pine cell culture following transformation. The bi-layer system comprises application of eradicants (such as carbenicillin, ticarcillin, cefotaxime, mixtures of these, or the like) in a thin film of liquid medium on top of the gelled support medium under the polyester or liquid-permeable fluoropolymer support membrane, or in liquid absorbed in a layer of filter paper between the gelled medium and the support membrane, thereby allowing the eradicants to pass through the support membrane into the cultured cells. This method can be used in addition to, or instead of, the stringent washing methods described in the first improvement above. The liquid medium used to incorporate the eradicants is similar in composition to the gelled medium on which the pine tissue is grown, except that gelling agents and adsorbing components may be omitted, and eradicants, such as antibiotics, for better permeation into the cells or at higher concentrations than can be administered in the gelled media may be added. This improved method of eradicating *Agrobacterium* from pine tissue cultures, using support membranes, can be employed with any tissue culture phase or step that does not involve the formation of roots into the culture medium. For example, the tissue culture method can be employed with a selection and/or eradication medium based on a maintenance medium, a proliferation medium, an embryo development medium, a maturation medium, or a regeneration medium.

Media components such as antibiotics can also constitute much of the cost of tissue culture of transformed cells. Thus, another advantage to our methods lies in the small volume of liquid medium that is required to apply the component of interest. For example, the pine tissue may be grown on the surface of 20–30 ml of gelled medium in a petri dish, but only a few milliliters of overlaying liquid eradicant medium at the same concentration is necessary to restrict growth of *Agrobacterium*. The liquid medium, rather than beading up as liquid might on the surface of a glass or plastic plate, spreads over the surface of the pine tissue and gelled medium and through the support membrane by simple surface tension. Thus, only a fraction of the amount of antibiotic need be employed in the improved bi-layer tissue culture method.

The flexibility of the bi-layer system may allow even more savings in eradicant. Unlike gelled media (which must often be made fresh some days before needed and in which the eradicants often have a short half-life), aliquots of liquid eradicant-containing media can be frozen almost indefinitely for use when required. Furthermore, after a transfer onto fresh gelled medium lacking incorporated eradicant, the cultures which would still suffer *Agrobacterium* regrowth are readily distinguishable from those which have already undergone sufficient eradication, whereas with eradicant incorporated in the medium these will not be distinguishable. If it can be determined which cultures are no longer contaminated, the eradicant that would have been used for them is spared; while a liquid eradicant overlay can be added without significant delay to those cultures requiring it.

Selected, healthy transformed cells are cultured using conventional techniques for somatic embryogenesis of Southern yellow pines and hybrids thereof, such as described in Becwar et al. (1990; 1995; 1996), Handley and Godbey (1996) and Handley (1999), to produce transgenic somatic embryos and to regenerate plants from the transgenic embryos, such as by germination of the somatic embryos. Transgenic plants of *Pinus* species are generated from selected healthy transformed cells in accordance with similar techniques or techniques known in the art for regenerating plants of these species.

In the transformation of certain species of Southern yellow pines, particularly certain elite lines and hybrids, it is desired to include ABA in some of the media. For example, a number of pine species including Southern yellow pines such as *P. taeda* and hybrids, selection is improved because the proliferative health of transformed tissue is increased by using ABA in one or more of the recovery and selection media. We hypothesized that concentrations of ABA of 5–90 mg/L in these media, which are based on the same nutrient composition as proliferation media, may be involved in the switch between proliferation and differentiation, preventing use of the nutrients in the media for precocious further differentiation, and favoring their redirection toward proliferation as a result. We further hypothesized that cells in a proliferative mode would be more able to withstand and recover from certain types of stresses that might be lethal to differentiating embryos, because proliferation can occur from smaller and less intact cell masses than can differentiation (differentiating cells normally lose their totipotency). This model predicts that cells maintained in a proliferative mode by concentrations of ABA of 5–90 mg/L should be better able to withstand and recover from the stresses of transformation. In line with our prediction, we were able to detect for the first time, solely in treatments containing ABA in the selection media, confirmed transformants from lines that normally show the precocious development and early decline characteristics. Thus, ABA is utilized in media for transformation of those Southern yellow pines which normally show precocious development and early decline characteristics.

It has been observed that in a number of experiments using *Agrobacterium* transformation methods, that ABA is important in order to obtain transformed embryogenic masses from certain embryogenic lines of some elite lines and hybrids of Southern yellow pines. For example, many more transformants (in more than 80% of the lines attempted) have been recovered from crosses with the elite *P. taeda* selection 7–56 as a parent, in which culture decline is frequently seen and transformed tissue had not been recovered. These transformed lines are seldom found in treatments that did not utilize ABA in the selection media. In contrast, multiple stable transformants were detected after selection in a treatment in which ABA had been added to the medium only during the first week of selection, and progressively more transformants were detected in treatments in which ABA was added to the selection medium during three, six, or nine weeks of the selection period. This result implies that the protective effect of the ABA which allows transformed cells to survive selection is already being exerted in the initial period of selection, but that it is beneficial throughout the selection period and that without it transformants are being lost before they can be detected. This result demonstrated that the previous failure to detect stable transformants from a particular cross with the parent 7–56 did not result from failure to transform any cells, but from failure of these transformed pine cells to grow during selection without ABA. These effects have been observed on media containing 5–30 mg/L ABA.

The present invention is generally useful for improving the growth of transgenic pine cell and embryogenic cultures.

The present invention is useful for improving selection of transformed cells by exposure of pine embryogenic cultures to selection agents (e.g. antibiotics and herbicides), following the application of transformation by *Agrobacterium*.

The present invention is further useful for eradication of *Agrobacterium* from pine embryogenic cultures.

The present invention is further useful for improving the exposure of pine embryogenic cultures to compounds used in selection of transgenic cultures after *Agrobacterium* transformation, such as selection agents, *Agrobacterium* eradicants, plant growth regulators and the like.

The present invention is further useful for improving facilitating the recovery of transformed embryogenic sublines from a diverse array of conifer embryogenic cultures subjected to transformation followed by selective growth, positive selection, or detection of transgenes.

EXAMPLES

The present invention is further described in the following examples, which are offered by way of illustration and are not intended to limit the invention in any manner. Standard techniques well known in the art or the techniques specifically described below are utilized.

Example 1

Preparation of Embryogenic Cultures, Transformation with *Agrobacterium*, and Eradication of the *Agrobacterium* Using Standard and Improved Wash Methods Loblolly pine (*Pinus taeda*) embryogenic cell lines were initiated from zygotic embryos of individual immature megagametophytes as previously described (Becwar et al. 1996). The procedure was as follows. Immature seed cones were collected from Westvaco's South Carolina coastal breeding orchards near Charleston, S.C. The seed cones were collected when the dominant zygotic embryo was at the precotyledonary stage of development. Using the classification system of von Arnold and Hakman (1988), the dominant zygotic embryo at this stage is referred to as being at stage 2; that is, an embryo with a prominent embryonic region with a smooth and glossy surface, subtended by elongated suspensor cells which are highly vacuolated. However, zygotic embryos at an earlier stage of development (stage 1) may also be used effectively to initiate embryogenic cultures.

For culture initiation intact seeds removed from seed cones were surface sterilized by treatment in a 10 to 20% commercial bleach solution (equivalent of a 0.525% to 1.050% sodium hypochlorite solution) for 15 minutes followed by three sterile water rinses (each of five minutes duration). Seeds were continuously stirred during the sterilization and rinsing process. Megagametophytes containing developing zygotic embryos were used as the explant for culture initiation. The seed coats of individual seeds were cracked open under a laminar-flow hood and the intact megagametophyte (which contains the developing zygotic embryos) was removed from the opened seed coat. Tissues attached to the megagametophyte, such as the megagametophyte membrane and the nucellus, were removed from the megagametophyte and discarded. The megagametophyte was placed on $DCR_1$ or $WV5_1$ initiation medium.

Basal salt mixtures proven effective for pine embryogenesis culture initiation include but are not limited to the DCR or WV5 basal salts formulations listed in Table 1. Complete media formulations used in initiation, maintenance and proliferative growth of pine embryogenic cultures in this and later Examples are listed in Table 2. The pH of the medium had been adjusted to 5.8 with KOH and HCl prior to autoclaving at 110 kPa (16 psi) and 121° C. for 20 minutes, and approximately 20 ml of medium had been poured into 100×15 mm sterile plastic petri dishes. Those skilled in the art of plant tissue culture will recognize that many other formulations, sterilization conditions, and media volumes would be applicable to the use of the present method.

TABLE 1

Basal Culture Media Formulations Used For Pine Embryogenesis

| COMPONENT | WV5[a] | DCR[b] | MSG[c] |
|---|---|---|---|
| | CONCENTRATION (mg/L) | | |
| INORGANIC SALTS | | | |
| $NH_4NO_3$ | 700.00 | 400.00 | 0 |
| $KNO_3$ | 259.00 | 340.00 | 100.00 |
| $Ca(NO_3)_2 \cdot 4H_2O$ | 963.00 | 556.00 | 0 |
| $MgSO_4 \cdot 7H_2O$ | 1850.00 | 370.00 | 370.00 |
| $KH_2PO_4$ | 270.00 | 170.00 | 170.00 |
| $CaCl_2 \cdot 2H_2O$ | 0 | 85.00 | 440.00 |
| KCl | 1327.00 | 0 | 745.00 |
| KI | 0.83 | 0.83 | 0.83 |
| $H_3BO_3$ | 31.00 | 6.20 | 6.20 |
| $MnSO_4 \cdot H_2O$ | 15.16 | 22.30 | 16.90 |
| $ZnSO_4 \cdot 7H_2O$ | 8.60 | 8.60 | 8.60 |
| $Na_2MoO_4 \cdot 2H_2O$ | 0.25 | 0.25 | 0.25 |
| $CuSO_4 \cdot 5H_2O$ | 0.25 | 0.25 | 0.03 |
| $CoCl_2 \cdot 6H_2O$ | 0.03 | 0.03 | 0.03 |
| $NiCl_2 \cdot 6H_2O$ | 0 | 0.03 | 0 |
| $FeSO_4 \cdot 7H_2O$ | 27.80 | 27.80 | 27.80 |
| $Na_2EDTA$ | 37.30 | 37.30 | 37.30 |
| VITAMINS, AMINO ACIDS | | | |
| Nicotinic acid | 0.50 | 0.50 | 0.50 |
| Pyridoxine.HCl | 0.50 | 0.50 | 0.10 |
| Thiamine HCl | 1.00 | 1.00 | 0.10 |
| Glycine | 2.00 | 2.00 | 0 |
| Glutamine[d] | 0 | 250.00 | 1450.00 |

[a]According to Coke (1996).
[b]According to Gupta and Durzan (1985).
[c]According to Becwar et al. (1990).
[d]Added as a filter-sterilized aqueous stock to autoclaved medium while still warm (about 60° C.).

TABLE 2

Initiation, Maintenance, And Proliferation Media Formulations Used For Pine Embryogenesis

| COMPONENT | Gelled Initiation Medium $WV5_1$ | Gelled Initiation Medium $DCR_1$ | Gelled Maintenance Medium $WV5_2$ | Gelled Maintenance Medium $DCR_2$ | Preparation Medium $DCR_3$ | Liquid[f] Proliferation Medium $DC_4$ |
|---|---|---|---|---|---|---|
| Basal medium[a] | WV5 | DCR | WV5 | DCR | DCR | DCR |
| | Concentration (g/L) | | | | | |
| Inositol | 0.50 | 0.50 | 0.50 | 0.50 | 0.50 | 0.50 |
| Casein hydrolysate[b] | 0.50 | 0.50 | 0.50 | 0.50 | 0.50 | 0.50 |
| L-glutamine | 0 | 0.25 | 0 | 0.25 | 0.25 | 0.25 |
| Sucrose | 0 | 30.00 | 30.00 | 30.00 | 0–60.00 | 30.00 |
| Maltose | 30.00 | 0 | 0 | 0 | 0–60.00 | 0 |
| Polyethylene glycol | 0 | 0 | 0 | 0 | 0–70.00 | 0 |
| GELRITE[c] | 1.5 | 1.5 | 2.00 | 2.00 | 0–6.00 | 0 |
| Activated Carbon | 0 | 0 | 0 | 0 | 0–0.5 | 0–0.5 |
| PHYTOHORMONES | | | | | | |
| Auxin[d] | 1.0–3.0 | 3.0 | 1.0–3.0 | 3.0 | 3.0 | 3.0 |
| Cytokinine[e] | 0.50 | 0.50 | 0.50 | 0.50 | 0.50 | 0.50 |
| Abscisic Acid | 10.00 | 10.00 | 10.00 | 10.00 | 0 | 0 |

[a]Refer to Table 1 for composition of basal medium.
[b]In some Examples, defined amino acid mixtures were substituted for casein hydrolysate.
[c]GELRITE ® (gellan gum manufactured by Merck, Inc.).
[d]2,4-dichlorophenoxyacetic acid (2,4-D) or naphthalene acetic acid (NAA).
[e]$N^6$-benzylaminopurine (BAP) or $N^6$-benzyladenine (BA).
[f]For all liquid culture media used in these examples, no gelling agent was added and the medium was stored in 500 ml batches under refrigeration or frozen prior to use.

After megagametophyte explants were placed in culture, the perimeter of the dish was sealed with two wraps of NESCOFILM® sealing film (commercially available from Karlan Company). The dishes were incubated in the dark at a constant temperature of 23° C.±2° C. After about 7 to 21 days, embryogenic tissue extruded from the micropyle of the megagametophyte explants. At six weeks following the placement of the explant on initiation media, tissue masses that had extruded and were proliferating from individual explants were isolated to individual petri plates on maintenance medium $DCR_2$ or $WV5_2$ and assigned line numbers. After one to three months of culture on maintenance medium, the tissue cultures were cryopreserved.

Specifically, the cells were added to an equal volume of liquid DCR medium containing sorbitol, for a final concentration of 0.2–0.4M sorbitol. Erlenmeyer flasks containing the resultant suspension were incubated for 24 hours in the dark on a gyrotory shaker (commonly at 100 rpm), and then placed on ice. Aliquots of the cryoprotectant dimethyl sulfoxide (DMSO) were added to the suspension to bring final concentration of DMSO to 10%. One milliliter aliquots of the cell suspension containing DMSO were then transferred to freezing vials, placed in a programmable freezer, and cooled to −35° C. at 0.33° C. per minute. The freezing vials were subsequently immersed in liquid nitrogen inside a cryobiological storage vessel for long-term storage. Those skilled in the art of plant tissue culture will recognize that other cryopreservation protocols would be applicable to the present method.

Frozen cultures were retrieved when desired by removing individual vials from the cryobiological storage vessel and placed in 42°±2° C. water to rapidly thaw the frozen cell suspensions. The thawed cell suspensions were aseptically poured from the cryovial onto a sterile 35 μm pore size polyester membrane support placed over sterile filter paper (WHATMAN® filter paper no. 2, Whatman International Ltd.) for a few minutes to allow the DMSO cryoprotectant solution to diffuse away from the embryogenic tissue into the paper. The embryogenic tissue on the polyester support membrane was then transferred to $DCR_2$ maintenance medium and incubated at 23° C. in the dark for 24 hours to allow additional DMSO to diffuse away from the tissue into the medium. The polyester support bearing the embryogenic tissue was then removed from the medium and transferred to fresh $DCR_2$ maintenance medium, and thereafter, every 14–21 days to a fresh plate until the amount of cells per plate reached about 1 g. The culture environment during post-cryopreservation recovery and growth was 23° C.±2° C. in the dark. Those skilled in the art will recognize that many different cryopreservation and recovery procedures would be suitable for use with this method and the detail in this example may not be construed to limit the application of the method.

After growth to sufficient mass on this medium as described above, the tissue cultures were placed in $DCR_4$ liquid maintenance medium (Table 2) containing activated carbon. Suspension cultures were established by inoculating a 250 ml Nephelo sidearm flask (Kontes Chemistry and Life Sciences Products) with 1 g of tissue from each of three genetically different tissue culture lines into 20 ml liquid $DCR_4$ medium. The flasks containing the cells in liquid medium were then placed on a gyrotory shaker at 100 rpm in a dark culture room at a temperature of 23° C.±2° C. One week later, the liquid in each flask was brought up to 35 ml by pouring 15 ml fresh medium into the culture flask and swirling to evenly distribute the cells. At 7-day intervals the cell growth was measured in the sidearm by decanting cells and medium into the sidearm portion of the flasks, allowing the cells to settle for 30 minutes and then measuring the settled cell volume (SCV). When the SCV was greater than or equal to half the maximal SCV (50% of the volume of the flask was occupied by plant cells), Suspension cultures were established as above. At 7-day intervals the cell growth was measured in the sidearm by decanting cells and medium into the sidearm portion of the flasks, allowing the cells to settle for 30 minutes and then measuring the SCV. When each suspension's SCV was greater than or equal to half the maximal SCV (50% of the volume of the flask was occupied by plant cells), it was split with half going into another sidearm 250 ml flask, and both flasks were brought up to 35 ml with fresh medium. When the SCV was greater than or equal to half the maximal SCV, each culture was transferred to a 500 ml sidearm flask containing a total of 80 ml cells and medium, for routine maintenance. The lines were maintained in culture in 500 ml sidearm flasks, splitting into additional flasks when necessary, for up to several months. All of them showed typical pine precotyledonary embryogenic cell culture morphology with long suspensor-like cells appending dense cytoplasmic head-type cells. Those skilled in the art will recognize that many different maintenance and proliferation procedures would be suitable for use with this method and the detail in this example may not be construed to limit the application of the method.

To prepare for gene transfer, nylon, polyester, and fluoropolymer membrane supports (Sefar) were sterilized by autoclaving and placed in separate sterile Buchner funnels, and one to five milliliters of pine embryogenic suspension was pipetted onto each support such that the embryogenic tissue was evenly distributed over its surface. Following this the liquid medium was suctioned from the tissues and each support bearing the embryogenic tissue was placed on gelled medium for inoculation by *Agrobacterium*. Genes were then introduced into the somatic embryogenic material by co-cultivation with *Agrobacterium*. Specifically, gene constructs containing a reporter gene and a selectable marker were introduced into *Agrobacterium* tumefaciens strain GV2260, the highly virulent strain EHA105, and EHA105 with the virulence-enhancing plasmid pTOK47 (Wenck et al. 1999), by techniques well known to those skilled in the art, and virulence was then induced with adminstration of acetosyringone by commonly used techniques, well known to those skilled in the art, whereupon the induced *Agrobacterium* was co-mingled with the plant material and these cells were co-cultivated in the dark at 23°±2° C. for approximately 24–72 hours. Those skilled in the art recognize that many different gene constructs, plasmids, strains, media, and co-cultivation times and protocols would be suitable for use in the present method.

Following co-cultivation, the eradication of *Agrobacterium* from the cultures was carried out as follows. The cells were re-suspended into fresh $DCR_4$ liquid wash medium (Table 2), which in some treatments contained eradicants such as 200–400 mg/L TIMENTIN® antibiotic, 250–500 mg/L carbenicillin, or 250–500 mg/L cefotaxime. Those skilled in the art of plant transformation will recognize that a variety of different eradicants may be used against *Agrobacterium*, and any of those are suitable for the present method. The $DCR_4$ liquid wash medium was contained in sterile containers comprising either conventional Erlenmeyer flasks, Nephelo sidearm flasks as described above, screw-top test tubes, MAGENTA® boxes with conventional lids or MAGENTA® aerated lids, "baby food" jars with conventional lids or MAGENTA® aerated lids, conventional beakers, or multi-well plates. Resuspension was initiated by grasping the membrane support bearing the infected cells, using forceps, and rolling or folding it so that it could be taken up and placed into the liquid in the wash container. The liquid was then agitated to get the cells into suspension, and the membrane support was scraped with sterile forceps if cells appeared to be adhering to it. Once the cells were in suspension, the membrane was removed with sterile forceps.

Following each wash step, the cells were plated onto fresh sterile support membranes of the same type as used in the previous step, again by placing the fresh sterile support membranes in a sterile Buchner funnel, pipetting the suspension of plant cells onto the membranes, and again suctioning the liquid medium from the tissues using a mild vacuum. In other treatments, the cells were plated onto fresh sterile support membranes of a different type at this time, for example cells previously plated on nylon were now plated on polyester. In this example, nylon and polyester membranes with dry mesh size of 35 microns and nylon, polyester, and fluoropolymer membranes with dry mesh size of 85 microns were used. We found that the bacterial cells are largely washed through the mesh of the fabric membrane support, while the much larger pine cells are retained. Thus, the maximum effective mesh size desirable for use in this method would depend on the size of the pine cells being cultured.

For each successive wash cycle, the cells were again resuspended in and briefly cultured in fresh sterile wash medium by agitating the membrane bearing the cells in the liquid, again removing cells that appeared to be adhering by gently scraping with forceps. The cells were then re-plated on fresh membrane supports over Buchner funnels. The presence of the bacteria in the collected post-rinse medium was observed both by its cloudy appearance and by counting colonies that arose from culturing it on a rich bacterial medium. This procedure was repeated for different numbers of wash cycles in order to determine experimentally after how many cycles the colony counts of the collected post-rinse medium would demonstrate that the *Agrobacterium* was eradicated, and after how many cycles the pine cells had become inviable (measured by lack of subsequent growth, presumably due to successive damage).

The results were that the cells were released very easily from the polyester and fluoropolymer support membranes, requiring no scraping, while the nylon membranes retained many cells and scraping was usually required for resuspension. Thus, more washes could be performed in an equivalent period of time when polyester or fluoropolymer supports were used, and the final amount of viable pine cells in culture after multiple washes, measured by settled cell volume as described above, remained closer to the initial amount.

Additionally, the pine cells remained viable for longer total durations of washes (up to five days in these experiments) in "baby food" jars with aerated lids, presumably due to crushing and loss of cells during the more cumbersome process of passing them through the narrower necks of tubes and flasks, the difficulty of maintaining axenicity in beakers, and due to the lesser aeration in vessels with corners, narrow volumes, or lacking aerated lids.

The improved washing method described in this example was capable of eradicating all three *Agrobacterium* strains used for inoculation, including the hypervirulent strain strain EHA105 with the virulence-enhancing plasmid pTOK47, without excessive damage to the pine cells, as measured by their ability to resume growth following completion of the bacterial eradication procedure.

To summarize, in washing procedures using either nylon, polyester or fluoropolymer support membranes for transferring the cells between the co-cultivation, wash, and post-wash culture media, bacterial colony counts from the cultured post-rinse medium showed that the number of colonies arising from *Agrobacterium* inoculum remaining after the washes decreased significantly after washing, allowing the growth of the remaining viable pine cells to proceed without the very rapid overgrowth by *Agrobacterium* observed in controls not washed with eradicant-containing medium. However, the pine cells were released more easily from the polyester and fluoropolymer support membranes, while the nylon membranes retained many cells, and scraping was usually required for resuspension. Thus, it seemed that more washes could be performed in an equivalent period of time when polyester or fluoropolymer supports were used, and the final amount of viable pine cells in culture after multiple washes remained closer to the initial amount. Additionally, there was less damage to pine cells, as measured by subsequent growth of the pine cells, when washes were performed in "baby food" jars with aerated lids. Washing in these jars was facilitated by the use of polyester or fluoropolymer supports due to the rapid release of the cells from these supports; merely dipping the support into the jar containing the wash medium before agitation sufficed to initiate washing, with the result that the cells were held for less time in unagitated (anaerobic) liquid.

Colony counts showed that the number of colonies arising from *Agrobacterium* inoculum remaining after the washes decreased significantly after washing, allowing the growth of the pine cells to proceed without the very rapid overgrowth by *Agrobacterium* which was observed in controls which were not washed with eradicant-containing medium.

Stable loblolly pine transformants were recovered when only a single rinse or a single overnight wash was carried out, but approximately twice as many transformants were recovered from four different loblolly pine lines when 2–3 short (1–12 hours) duration washes were used. We also observed that continued *Agrobacterium* regrowth in treatments that received only a single wash was much greater under the nylon support membranes than under the polyester support membranes. Thus, not only was the process of carrying out multiple washes greatly facilitated by the use of polyester supports to resuspend the tissue for each wash, but the polyester supports did not appear to retain as much *Agrobacterium* that could subsequently regrow on the pine tissue. This may also be due to swelling of the nylon fibers, impeding the passage of *Agrobacterium* cells as the plant tissue is rinsed.

Stable loblolly pine transformants were recovered following the use of either nylon, polyester, or fluoropolymer supports for the washes carried out in wide-mouthed vessels as described. However, the number of transformants recovered using polyester or fluoropolymer supports was 5–6 times greater than when nylon supports were used, and greatest using fluoropolymer supports for the washes. Some loblolly pine lines produced stable transformants only when polyester or fluoropolymer supports were used.

Plants could not be regenerated from transgenic pine lines that were treated using a stringent washing process involving multiple lengthy washes to obtain complete eradication of the *Agrobacterium*, using nylon membranes for cell collection. Plants have subsequently been regenerated from transgenic pine lines recovered using this improved eradication process, with fewer washes of shorter duration facilitated by use of the supports in the method disclosed here following *Agrobacterium* transformation.

Example 2

Growth and Development of Pine Cells on Membrane Supports Over Gelled Media

Embryogenic cell lines of *P. taeda*, as well as cell lines of hybrids between *P. taeda* and *P. rigida*, used in this example, were generated by the methods described in the above example. Two hundred proliferating culture lines were selected for use in this study and randomly assigned to one of two treatments using a very small amount of tissue, to simulate the situation following identification of a transformation event on selection:

A: Approximately 0.1 g of tissue was placed directly onto the surface of the gelled maintenance medium.

B: Approximately 0.1 g of tissue was placed onto a polyester support membrane (SEFAR PeCap® fabric support Catalog No. 7-35/11) cut to 55 mm square, laid on the surface of the gelled maintenance medium.

Every two weeks the culture was transferred to fresh medium. This simulates regular transfers of transformed cells that are being selectively proliferated on selection medium, e.g. in preparation for cryopreservation or embryo development/maturation for regeneration. Cells that stuck to or were embedded in the surface of the media could not be transferred. Any obviously necrotic cells were also discarded. Minor culture loss due to contamination resulted in a total of 96 lines being evaluated for Treatment A, and 98 lines being evaluated for Treatment B. Beginning four weeks after start of the experimental treatments, cultures were examined weekly and data taken on the number that had reached a target mass of at least 2 grams. When cultures reached a total cell mass of at least 2 grams, or when cultures were discarded for reasons of culture decline, the date was recorded. The experiment was terminated after 10 weeks.

There was a significant treatment effect on the number of lines that grew to a total mass of at least 2 grams within this period (Table 3). In the treatment using support membranes (Treatment B), 39 of 98 lines grew to at least 2 grams, while only 17 of 96 lines growing directly on the gelled medium reached 2 grams.

TABLE 3

Number Of Embryogenic Cultures That Grew To At Least 2 g, Using Each Of Two Maintenance Methods

| Maintenance Method | Starting Cell Lines | Cell Lines reaching 2 g |
|---|---|---|
| Directly on medium | 96 | 17 |
| On polyester support | 98 | 39 |

More cultures were successful (attained a mass of 2 g) when maintained on support membranes because the tissues grew more quickly than those maintained directly on the surface of the media. In addition, the number of weeks between the first and last cultures attaining 2 grams was less for cultures maintained on support membranes (3 weeks) than for those maintained directly on the surface of the medium (5 weeks).

In general, on the support membranes over maintenance/proliferation media, cell morphology appeared much healthier. When maintained directly on the surface of the medium, cells in the center of the clumps often became necrotic, probably due to anaerobic conditions and barriers to diffusion of nutrients and plant growth regulators from the medium. Maintenance of the tissue in a layer over the polyester support membrane reduced the amount of such non-specific tissue necrosis, and therefore, a larger percentage of the tissues were vigorous.

For tests of the effects of different types of membranes on growth and proliferation of pine embryogenic cells, each of the lines was plated on $DCR_2$ maintenance/proliferation medium over different membrane support treatments. The treatments were as shown in Table 4. A range of fiber types (which corresponded to different liquid absorption and resistance characteristics) and mesh sizes was tested; in theory, pore sizes from 0.2 microns up to about half the size of the cells being cultured could be used, to allow permeability to liquid medium and complex organic molecules without loss of the cultured cells through the mesh. The membranes being tested were available in a range of thicknesses and displayed variation in other characteristics such as thread size and percentage open area, as shown in Table 4 below.

TABLE 4

Properties Of Membrane Supports Tested In Example 2

| Treatment code | Fiber type[1] | % open area[2] | Mesh opening[3] | Mesh/cm[4] | Thread diameter (microns) | Membrane thickness (microns) | SEFAR Catalog No.[5] |
|---|---|---|---|---|---|---|---|
| A | n | 9.5 | 15 | 202 | 35 | 60 | N 3-15/10 |
| B | n | 16 | 35 | 100 × 128 | 35 | 97 | N 3-35/16 |
| C | n | 22 | 58 | 82 | 65 | 110 | N 3-58/22 |
| D | n | 30 | 63 | 71 × 94 | 43 | 95 | N 3-63/30 |
| E | n | 21 | 74 | 61 | 89 | 155 | N 3-74/21 |
| F | n | 34 | 85 | 65 × 74 | 50 | 98 | N 3-85/30 |
| G | p | 45 | 118 | 52 × 59 | 40/64 | 106 | P 7-118/45 |
| H | p | 12 | 21 | 163 | 41 | 70 | P 7-21/12 |
| I | p | 21 | 30 | 173 | 28 | 50 | P 7-30/21 |
| J | p | 21 | 35 | 150 | 33 | 65 | P 7-33/21 |
| K | p | 11 | 35 | 92 | 64 | 125 | P 7-35/11 |
| L | p | 36 | 51 | 119 | 33 | 65 | P 7-51/36 |
| M | p | 20 | 52 | 90 | 55 | 101 | P 7-52/20 |
| N | p | 33 | 59 | 97 | 44 | 65 | P 7-59/33 |
| O | p | 39.5 | 73 | 87 | 43 | 65 | P 7-73/40 |
| P | E | 27 | 85 | 61 | 80 | 157 | F 9-85/27 |

[1]N = nylon fiber mesh which absorbed 3.8 to 4.0% liquid from underlying media. The mesh's resistance to citric acid was conditional. P = polyester fiber mesh which absorbed 0.4% liquid from underlying media. The mesh's resistance to citric acid was satisfactory under all conditions. E = ethylene tetrafluoroethylene fiber mesh which did not absorb any liquid from underlying media. The mesh's resistance to citric acid was satisfactory under all conditions.
[2]Percent open area in dry membrane.
[3]Mesh opening in dry membrane (microns).
[4]Some support types were generated using a 3:1 taffeta weave rather than a 1:1 straight or twill weave, resulting in two measurements for mesh/cm. In these experiments, as can be seen by comparison of Table 4 above with Tables 6 and 7 below, the independent effect of the weave type was not found to be significant.
[5]N = NITEX ®; P = PECAP ®; F = FLUORTEX ®.

Three replicate plates were generated from each cell line for each of the treatments. For each plate, a sterile 55×55 mm square membrane support of the type listed for the corresponding treatment was placed in a sterile Buchner funnel. Suspension culture cells and medium, measured by SCV to give an equivalent amount of cells for each cell line, were pipetted onto each membrane support. The liquid medium was then suctioned from the cells using a mild vacuum. Each membrane support with cells was removed from the Buchner funnel and placed on DCR$_2$ maintenance/proliferation medium (Table 2). Petri dishes were incubated in a dark growth chamber at 23°±2° C. The membrane supports bearing the cells were then transferred to new petri dishes containing fresh medium every 2–3 weeks. Growth of the cells was measured in grams using a sterile milligram balance. The results are shown in Table 5 below.

TABLE 5

Growth And Proliferation Of Embryogenic Cell Cultures On Different Types Of Support Membranes

| | | Gain in tissue weight in grams on proliferation medium over membrane support | |
|---|---|---|---|
| Line[1] | Treatment[2] | in two weeks | in six weeks |
| L1 | A | 2.790 ± 0.763 | 7.467 ± 0.696 |
| L2 | A | 4.590 ± 1.181 | 9.833 ± 0.964 |
| H1 | A | 2.470 ± 1.310 | 7.843 ± 2.013 |
| L1 | B | 0.800 ± 0.165 | 3.637 ± 0.212 |
| L2 | B | 3.260 ± 0.452 | 9.407 ± 1.138 |
| H1 | B | 2.730 ± 0.062 | 7.850 ± 0.433 |
| L1 | C | 2.867 ± 0.283 | 6.750 ± 0.877 |
| L2 | C | 4.240 ± 1.005 | 9.507 ± 0.640 |
| H1 | C | 3.523 ± 0.316 | 9.817 ± 0.546 |
| L1 | D | 2.497 ± 0.514 | 6.583 ± 0.663 |
| L2 | D | 4.687 ± 0.465 | 8.723 ± 0.604 |

TABLE 5-continued

Growth And Proliferation Of Embryogenic Cell Cultures On Different Types Of Support Membranes

| | | Gain in tissue weight in grams on proliferation medium over membrane support | |
|---|---|---|---|
| Line[1] | Treatment[2] | in two weeks | in six weeks |
| H1 | D | 3.237 ± 0.354 | 8.910 ± 0.816 |
| L1 | E | 1.520 ± 0.296 | 4.533 ± 0.516 |
| L2 | E | 4.660 ± 0.262 | 9.760 ± 1.612 |
| H1 | E | 3.547 ± 0.214 | 9.137 ± 0.142 |
| L1 | F | 2.840 ± 0.288 | 6.557 ± 0.441 |
| L2 | F | 4.820 ± 0.377 | 9.400 ± 1.048 |
| H1 | F | 3.087 ± 0.912 | 8.687 ± 0.624 |
| L1 | G | 2.220 ± 0.265 | 5.133 ± 0.429 |
| L2 | G | 3.970 ± 0.655 | 9.537 ± 1.131 |
| H1 | G | 3.207 ± 0.420 | 7.893 ± 0.722 |
| L1 | H | 3.043 ± 0.511 | 6.247 ± 1.123 |
| L2 | H | 4.610 ± 0.560 | 10.717 ± 0.964 |
| H1 | H | 3.957 ± 0.483 | 8.913 ± 0.873 |
| L1 | I | 3.383 ± 0.581 | 6.563 ± 0.559 |
| L2 | I | 4.560 ± 1.079 | 10.557 ± 0.644 |
| H1 | I | 3.970 ± 0.205 | 8.427 ± 0.369 |
| L1 | J | 2.907 ± 0.244 | 6.537 ± 0.746 |
| L2 | J | 4.753 ± 1.193 | 10.803 ± 0.609 |
| H1 | J | 3.270 ± 1.264 | 8.640 ± 1.618 |
| L1 | K | 2.660 ± 0.400 | 5.997 ± 0.347 |
| L2 | K | 4.697 ± 0.376 | 9.607 ± 0.774 |
| H1 | K | 3.207 ± 1.018 | 9.040 ± 0.439 |
| L1 | L | 2.690 ± 0.384 | 6.250 ± 0.265 |
| L2 | L | 4.513 ± 1.366 | 10.370 ± 1.710 |
| H1 | L | 2.947 ± 0.591 | 9.177 ± 0.996 |
| L1 | M | 2.603 ± 0.286 | 6.307 ± 0.813 |
| L2 | M | 3.900 ± 0.252 | 9.477 ± 0.206 |
| H1 | M | 3.217 ± 0.324 | 9.230 ± 1.178 |
| L1 | N | 2.957 ± 0.391 | 5.967 ± 0.788 |
| L2 | N | 3.927 ± 0.903 | 9.523 ± 0.715 |

TABLE 5-continued

Growth And Proliferation Of Embryogenic Cell Cultures On Different Types Of Support Membranes

| | | Gain in tissue weight in grams on proliferation medium over membrane support | |
|---|---|---|---|
| Line[1] | Treatment[2] | in two weeks | in six weeks |
| H1 | N | 3.607 ± 0.798 | 8.163 ± 2.025 |
| L1 | O | 3.107 ± 0.706 | 7.473 ± 1.541 |
| L2 | O | 4.590 ± 1.208 | 10.617 ± 1.267 |
| H1 | O | 3.723 ± 0.725 | 11.007 ± 0.180 |
| L1 | P | 2.213 ± 0.519 | 5.727 ± 0.595 |
| L2 | P | 4.943 ± 0.267 | 10.477 ± 0.818 |
| H1 | P | 3.247 ± 0.131 | 8.953 ± 0.934 |

[1]L1 = *P. taeda* cell line 1; L2 = *P. taeda* cell line 2; H1 = hybrid pine cell line 1.
[2]See Table 5.

After the cell masses had been allowed to proliferate for six weeks, they were resuspended in $DCR_3$ liquid medium again as described above, and re-plated on fresh membrane supports of the same treatment as used during proliferation. Three replicate plates were generated from each of two embryogenic cell lines (one *P. taeda* line and one hybrid pine line) for each of the treatments. When the cell suspensions had been brought to approximately identical (half-maximal) SCV, equivalent amounts of suspension culture cells were pipetted onto sterile 55×55 mm square membrane supports of the type listed for each corresponding treatment as above, for placement on $MSG_1$ development/maturation medium (Table 6) to assess the ability of the cultures to develop high quality harvestable stage 3 (cotyledonary) embryos. Dishes were incubated in a dark growth chamber at 23±2° C. The membrane supports were then transferred to new petri dishes containing fresh medium every 3 weeks. At week 9, stage 3 (cotyledonary) embryos were counted and those deemed suitable for germination were harvested. Results are shown in Table 7 below.

TABLE 6

Composition Of Development/Maturation And Germination Media Used For Pine Embryogenic Cells

| COMPONENT | Development/ Maturation Medium $MSG_1$ | Pre- Germination Medium $MSG_2$ | Germination Medium $MSG_3$ |
|---|---|---|---|
| Basal medium[a] | MSG | MSG | MSG |
| | CONCENTRATION (g/L) | | |
| Ammonium Nitrate | 0 | 0 | 0.80 |
| Inositol | 0.10 | 0.10 | 0.10 |
| L-glutamine | 1.45 | 1.45 | 0 |
| Sucrose | 0 | 0 | 30.00 |
| Maltose | 60.00 | 60.00 | 0 |
| GELRITE[b] | 2.00 | 2.00 | 2.00 |
| Activated Carbon | 0–1.25 | 0 | 5.00 |
| PEG[c] | 0–100.00 | 0 | 0 |
| ABA[d] | 11–150 | 21 | — |

[a]Refer to Table 1 for composition of basal medium.
[b]GELRITE ® (gellan gum manufactured by Merck, Inc.).
[c]Polyethylene glycol (molecular weight of 4000).
[d]Abscisic acid.

TABLE 7

Average number of embryos produced on replicate plates of tissue placed over development medium on various types of support membranes

| Line 1 | Treatment[1] | Embryos produced |
|---|---|---|
| *P. taeda* | A | 76.7 ± 46.2 |
| Hybrid | A | 155.7 ± 26.7 |
| *P. taeda* | B | 44.7 ± 11.4 |
| Hybrid | B | 169.3 ± 7.2 |
| *P. taeda* | C | 24.0 ± 6.2 |
| Hybrid | C | 101.3 ± 20.5 |
| *P. taeda* | D | 56.3 ± 31.2 |
| Hybrid | D | 137.0 ± 18.1 |
| *P. taeda* | E | 52.0 ± 33.1 |
| Hybrid | E | 103.7 ± 90.4 |
| *P. taeda* | F | 25.0 ± 13.2 |
| Hybrid | F | 123.7 ± 14.6 |
| *P. taeda* | G | 165.3 ± 29.0 |
| Hybrid | G | 169.0 ± 33.4 |
| *P. taeda* | H | 42.7 ± 9.1 |
| Hybrid | H | 135.0 ± 23.6 |
| *P. taeda* | I | 34.7 ± 4.2 |
| Hybrid | I | 129.7 ± 9.3 |
| *P. taeda* | J | 34.3 ± 7.4 |
| Hybrid | J | 75.3 ± 20.7 |
| *P. taeda* | K | 34.7 ± 9.5 |
| hybrid | K | 185.7 ± 27.3 |
| *P. taeda* | L | 101.7 ± 9.1 |
| hybrid | L | 213.3 ± 25.7 |
| *P. taeda* | M | 26.0 ± 6.6 |
| hybrid | M | 149.3 ± 28.0 |
| *P. taeda* | N | 148.0 ± 64.6 |
| hybrid | N | 147.7 ± 13.6 |
| *P. taeda* | O | 34.0 ± 58.9 |
| hybrid | O | 156.7 ± 33.0 |
| *P. taeda* | P | 192.7 ± 58.8 |
| hybrid | P | 191.7 ± 14.5 |

[1]Treatment according to Table 4.

Embryos harvested from the development medium were again placed on membrane supports to facilitate bulk transfer of embryos through the preparatory steps for germination. The membrane supports, bearing around 25–40 harvested embryos each, were placed over gelled medium $MSG_2$ (Table 6), in petri plates and incubated for about four weeks in the dark at a temperature of 4° C. Next, the membrane supports still bearing the embryos were placed in sealed containers at 100% relative humidity for about three weeks in the dark at a temperature of 23°±2° C. Next, the membrane supports still bearing the embryos were transferred to medium $MSG_3$ (Table 6) and incubated for about three days in the dark at a temperature of 23°±2° C. Embryos were then removed from their membrane supports and placed individually onto the surface of fresh $MSG_3$ medium in petri plates for germination in the light at a temperature of 27°±3° C. Germination plates were examined weekly, over a period of about four weeks. Despite the differences in the number of embryos developed to a harvestable quality on the different types of membranes, an experiment using three embryogenic lines demonstrated that the percentage of those embryos that could be germinated was not significantly different.

As seen from the data shown in Tables 4, 5, and 7, the characteristic of the different membrane treatments that had the largest effect on proliferative growth of embryogenic cells was the degree to which the support membrane itself absorbed or reacted with liquid from the media below it, resulting in swelling of the fibers making up the membrane. Membranes made of less absorbent and less acid-reactive materials (those made of polyester and ETFE) generally promoted better growth, perhaps because in failing to absorb as much liquid, they allow more of the liquid and the large molecules contained in it, such as plant growth regulators, to pass through the membrane and enter the pine tissue. This characteristic of the polyester and ETFE membranes also had a strongly significant promotive effect on regeneration of high quality embryos from the embryogenic cell lines when the cultures were both maintained/proliferated and embryos developed/matured on the same type of membrane sequentially.

It had been expected that mesh size, and factors affecting it, might have a significant effect on growth or development. However, the data show that there were no significant correlations between either the number of fibers per cm of the membrane or the dry mesh opening size with either growth or embryo development. The values supplied by the manufacturer for mesh size and percent open area of the membrane when dry were considered independently of the capacity of the fibers to absorb liquid and swell (particularly in the nylon membranes, this would decrease both the effective mesh size and percent open area measurements). There was also no correlation between the percent open area and growth, while with embryo development there was only a weak correlation (R<0.35) with the percentage open area.

Similarly, other characteristics, such as the thickness of the membranes or the dry diameter of the individual fibers making up the membranes, did not appear to have any significant effect either on growth of the cultures or development of harvestable embryos when considered independently of the fiber type. Thread diameter had a significant effect only when considered within fiber type; both proliferative growth and embryo development/maturation were best on polyester or ETFE membranes with greater than 40 micron fiber diameter, but because the ETFE membranes were, at the time this experiment was done, only available in the largest fiber diameter class, an apparent promotive effect for the larger fiber diameter class is likely to be confounded with fabric type and absorbance.

Finally, we found that the use of the membrane supports greatly facilitated the transfer of pine cell material between different media and culture phases. While the use of nylon supports had previously been claimed to facilitate the transfer of plant material, we found that removal of embryos at the harvest stage and germination stage described above was easier when supports made of non-swelling fibers (e.g. polyester) were used than when nylon was used. The use of any of these types of support membranes did not have any long-term adverse effects on germinability of the embryos harvested.

Thus, any of the fiber types could be used in supports to grow and develop embryos, but the main significant effect is one of absorbance characteristics of the type of fiber used in the membrane supports, namely that non-absorbent, non-acid-reactive fibers in liquid-permeable membrane supports (polyester or the fluoropolymer ETFE, in this example) resulted in best proliferation, best embryo differentiation, and easiest transfer.

Example 3

Use of a Biphasic System to Improve Eradication of *Agrobacterium*

Loblolly and hybrid pine cell lines which had been grown and maintained as described in Examples 1–2 above were used in this example. Support membranes bearing pine tissue were placed on gelled $DCR_2$ maintenance media with various antibiotics (cefotaxime or TIMENTIN® antibiotic) incorporated into the gelled $DCR_2$ maintenance media, or into liquid $DCR_4$ pipetted in a thin film over gelled $DCR_2$ maintenance media lacking antibiotics, or into liquid $DCR_4$ which was saturated into a filter paper laid on gelled $DCR_2$ maintenance media lacking antibiotics. Support membranes bearing control cells were placed either on gelled $DCR_2$ maintenance media, over liquid $DCR_4$ pipetted in a thin film over gelled $DCR_2$ maintenance media lacking antibiotics, or over a filter paper saturated with liquid $DCR_4$ and laid on gelled $DCR_2$ maintenance media lacking antibiotics. The eradication treatments and controls were continued for a period of approximately 12 weeks, with transfer of the polyester support membranes, bearing the pine embryogenic cells, every 14–21 days.

Results showed that the maintenance and proliferative culture of cells over a bi-layer formed by liquid $DCR_4$, in some treatments containing the eradicant antibiotics, pipetted in a thin film (1–3 ml, usually 1.5 ml) over gelled $DCR_2$ maintenance media, or saturated into a filter paper laid on gelled $DCR_2$ maintenance media, was not detrimental (and for some cell lines even appeared to be beneficial) to the growth of embryogenic cells, either of loblolly pine (4 lines from two unrelated families, designated with "P") or hybrid pine (lines designated "H") as seen in Table 8 below.

TABLE 8

Growth Of Pine Embryogenic Cells On Polyester Membrane Supports Over Biphasic Culture Media (Gelled Phase Under Liquid Phase)

Average growth over a one-month period (two transfers)

| Cell Line[1] | No liquid phase[2] | Liquid phase[3] | Liquid phase with cefotaxime[4] | Liquid phase with TIMENTIN ®[5] |
|---|---|---|---|---|
| P1 | 5.53 + 0.98 | 7.24 + 0.20 | 7.20 + 0.28 | 7.71 + 0.42 |
| P2 | 2.03 + 0.17 | 2.37 + n.d. | 1.93 + 0.24 | 2.58 + 0.09 |
| P3 | 5.27 + 2.62 | 9.36 + 0.25 | 6.75 + 0.25 | 9.00 + 0.56 |
| P4 | 2.84 + 0.40 | 11.18 + 0.34 | 8.97 + 0.19 | 10.79 + 0.90 |
| H1 | 4.53 + 0.73 | 5.82 + 0.29 | 4.53 + 0.28 | 5.73 + 0.52 |
| H2 | 5.43 + 0.59 | 11.34 + 0.66 | 8.76 + 0.63 | 11.58 + 0.67 |

[1]P1 = *P. taeda* cell line 1, P2 = *P. taeda* cell line 2, P3 = *P. taeda* cell line 3, P4 = *P. taeda* cell line 4, H1 = Hybrid pine cell line 1, H2 = Hybrid pine cell line 2.
[2]Non-biphasic.
[3]Liquid phase same medium as gelled phase except without gelling agent.
[4]Liquid phase containing 500 mg/L of cefotaxime.
[5]Liquid phase containing 400 mg/L of TIMENTIN ®.

Comparison with the non-biphasic control shows that the biphasic method was also not detrimental (and for some cell lines even appeared to be beneficial) to the embryogenicity of the cultures, as the results showed when pine cell cultures maintained in the treatments described above were subsequently transferred to embryo development medium $MSG_1$ as described in Example 2 (Table 9).

TABLE 9

Embryogenicity Of Cultures Submitted To Biphasic
Maintenance Treatments Prior To The Onset Of Embryo Development

| | Average Number Of Embryos Harvested Per Plate | | | |
|---|---|---|---|---|
| Cell Line[1] | No liquid phase[2] | Liquid phase[3] | Liquid phase with cefotaxime[4] | Liquid phase with 400 mg/L TIMENTIN ®[5] |
| P1 | 45.7 ± 31.4 (40%) | 39.7 ± 12.1 (15%) | 87.0 ± 37.5 (10%) | 101.0 ± 41.6 (64%) |
| P2 | 110.0 ± 29.6 (60%) | 94.3 ± 26.1 (35%) | 81.7 ± 44.5 (66%) | 85.5 ± 3.5 (80%) |
| P3 | 33.0 ± 5.6 (13%) | 12.0 ± 10.4 (11%) | 14.3 ± 4.2 (21%) | 58.7 ± 14.4 (65%) |
| P4 | 9.3 ± 2.5 (13%) | 76.3 ± 36.1 (28%) | 34.0 ± 16.1 (36%) | 56.7 ± 15.0 (30%) |
| H1 | 46.3 ± 18.2 (50%) | 122.7 ± 26.6 (87%) | 152.0 ± 40.8 (96%) | 151.5 ± 21.9 (88%) |
| H2 | 73.3 ± 7.23 (93%) | 119.3 ± 76.9 (93%) | 77.0 ± 10.4 (88%) | 118.0 ± 27.2 (85%) |

[1]P1 = P. taeda cell line 1, P2 = P. taeda cell line 2, P3 = P. taeda cell line 3, P4 = P. taeda cell line 4, H1 = Hybrid pine cell line 1, H2 = Hybrid pine cell line 2.
[2]Non-biphasic.
[3]Liquid phase same medium as gelled phase except without gelling agent.
[4]Liquid phase containing 500 mg/L of cefotaxime.
[5]Liquid phase containing 400 mg/L of TIMENTIN ®.

In a further test, this time using pine cells treated with *Agrobacterium* as described in Example 1 above, that therefore did require eradication, were plated on the treatments described above. In this case, eradicants used were TIMENTIN® antibiotic at higher concentrations (either 400, 500 or 800 mg/L) and AUGMENTIN® antibiotic at 500 mg/L. Eradicants presented to the cells in liquid $DCR_4$ pipetted in a thin film over gelled $DCR_2$ maintenance media, or saturated into a filter paper laid on gelled $DCR_2$ maintenance media were as or more successful in suppressing the growth of *Agrobacterium* than eradicants incorporated in the gelled $DCR_2$ media, with the overall use of only 7.5% of the amount of eradicant per plate in which it was applied (1.5 ml liquid vs. 20 ml gelled medium).

Similar to the results with non-transformed cells shown in Table 8 above, in this further test maintenance and proliferative culture of cells over a bi-layer formed by liquid $DCR_4$, in some treatments containing the eradicant antibiotics, pipetted in a thin film (1–3 ml, usually 1.5 ml) over gelled $DCR_2$ maintenance media, or saturated into a filter paper laid on gelled $DCR_2$ maintenance media, was not significantly detrimental (and in some cases even appeared to be beneficial) to the growth of embryogenic cells, as seen in Table 10 below.

TABLE 10

Growth Of Pine Embryogenic Cells On Polyester Membrane
Supports, Either Over Gelled Maintenance Media Containing Eradicants
or Over Biphasic Maintenance Media (Gelled Phase Under Liquid Phase)

| | Average growth over a six-week period (three transfers) | | |
|---|---|---|---|
| | P1[1] | P2[1] | P3[1] |
| Gelled media containing 500 mg/L TIMENTIN ® | 11.29 +/− 1.10 | 7.38 +/− 1.33 | 2.68 +/− 0.21 |
| Gelled media containing 800 mg/L TIMENTIN ® | 11.41 +/− 0.66 | 7.94 +/− 1.48 | 2.92 +/− 0.15 |
| Gelled media containing 500 mg/L AUGMENTIN ® | 11.15 +/− 1.41 | 9.44 +/− 0.81 | 4.04 +/− 0.10 |
| Biphasic treatment 1[2] | 12.53 +/− 3.44 | 9.81 +/− 0.73 | 6.88 +/− 0.25 |
| Biphasic treatment 2[3] | 9.95 +/− 0.89 | 8.97 +/− 1.00 | 5.14 +/− 0.20 |
| Biphasic treatment 3[4] | 8.97 +/− 4.14 | 8.30 +/− 1.41 | 6.45 +/− 0.49 |

[1]P1 = P. taeda cell line 1, P2 = P. taeda cell line 2, P3 = P. taeda cell line 3
[2]Liquid phase same medium as gelled phase except without gelling agent, and with 500 mg/L TIMENTIN added.
[3]Liquid phase same medium as gelled phase except without gelling agent, and with 800 mg/L TIMENTIN added.
[3]Liquid phase same medium as gelled phase except without gelling agent, and with 500 mg/L AUGMENTIN added.

These cell lines also demonstrated that embryo formation was not significantly different whether these eradicants were incorporated into the gelled medium or into a liquid phase in a bilayer system.

Furthermore, the flexibility of the bi-layer liquid eradicant surface application method allowed even more savings in eradicant. Unlike gelled media (which must be made fresh some days before needed and in which the eradicants have a short half-life), aliquots of liquid eradicant-containing media can be frozen almost indefinitely for use when required. After a transfer onto fresh gelled medium lacking incorporated antibiotic, the cultures that still contained *Agrobacterium* capable of regrowth were readily distinguishable from those that had been decontaminated. If eradicant was incorporated in the all media, decontaminated cultures are not distinguishable from those that were still contaminated with *Agrobacterium*. When, as with the improved method, it could be rapidly determined which cultures are no longer contaminated, the antibiotic that would have been used for them could be left out of the culture simply by not adding the liquid phase over the gelled maintenance medium, while a liquid eradicant overlay can be added without significant delay to those cultures requiring it.

*Agrobacterium* contamination has been reported as recurring sometimes after long periods of time. With many species, eradicants are incorporated in all culture media used after the initial infection, including selection media, proliferation media, media to induce the formation of organs or the development of somatic embryos, media to elongate or mature organs or embryos that are formed, and regeneration media. For pine embryogenic cells, incorporation of eradicants into the embryo development and maturation media has been difficult due to the high temperature of polymerization of the media resulting from the incorporation of a high level of polyethylene glycol. Therefore, loblolly and hybrid pine cell lines grown and maintained as described in Examples 1–2 above were placed on polyester support membranes over gelled $MSG_1$ embryo development and maturation media as described in Example 2 above, except that some of the development and maturation media were overlaid with various eradication treatments under the polyester support membranes. The treatments consisted of either no liquid phase, or a liquid phase identical to the gelled phase (except that gelling agent and activated charcoal were omitted) and incorporating either cefotaxime or TIMENTIN® antibiotic as an eradicant. Three replicate plates were generated from each of six embryogenic cell lines (two from each of two *P. taeda* families and one hybrid pine family) for each of the treatments, and assessed for the ability of the cultures to develop high quality harvestable stage 3 embryos. Dishes were incubated in a dark growth chamber at 23±2°C. The membrane supports were transferred to new petri dishes containing fresh medium every 3 weeks. At week 9, stage 3 embryos were counted and those deemed suitable for germination were harvested. The results are shown in Table 11 below.

TABLE 11

Effect Of Placing Cells On Polyester Support Membranes Over Erradicants In Liquid Phase of Biphasic Embryo Development and Maturation Media

| Cell Line[1] | No liquid phase[2] | Liquid phase with cefotaxime[3] | Liquid phase with 400 mg/L TIMENTIN ®[4] |
|---|---|---|---|
| P1 | 36.0 ± 7.6 | 208.0 ± 94.8 | 226.0 ± 67.9 |
| P2 | 94.0 ± 38.9 | 269.0 ± 23.3 | 217.0 ± 62.9 |
| P3 | 28.0 ± 17.7 | 25.0 ± 17.7 | 26.0 ± 7.8 |
| P4 | 103.0 ± 49.5 | 18.0 ± 1.0 | 16.0 ± 7.0 |
| H1 | 173.0 ± 31.8 | 200.0 ± 51.2 | 233.0 ± 10.1 |
| H2 | 166.0 ± 67.1 | 210.0 ± 67.1 | 300.0 ± 24.9 |

Number of Harvestable Cotyledonary Stage Embryos Developed Over

[1]P1 = *P. taeda* cell line 1, P2 = *P. taeda* cell line 2, P3 = *P. taeda* cell line 3, P4 = *P. taeda* cell line 4, H1 = Hybrid pine cell line 1, H2 = Hybrid pine cell line 2.
[2]Non-biphasic (gelled phase only).
[3]Liquid phase containing 500 mg/L of cefotaxime.
[4]Liquid phase containing 400 mg/L of TIMENTIN ®.

As shown in Table 11, the application of eradicants in a liquid phase between the gelled medium and the cells borne on a polyester support membrane does not result in detriment to embryo development in five of the six embryogenic lines (in fact, it appears to be beneficial in most of the lines), and embryos could be developed from all lines tested.

Embryos developed during biphasic application of eradicants as described in the paragraph above were subjected to a germination test to determine whether the biphasic application of eradicants under polyester support membranes over gelled $MSG_1$ embryo development and maturation media had affected their germinability. The treatments during embryo development consisted of either no liquid phase, or a liquid phase identical to the gelled phase (except that gelling agent and activated charcoal were omitted), or the same liquid phase incorporating either 200 or 400 mg/L TIMENTIN® antibiotic as an eradicant. Germination was carried out as described in Example 2, and the results are shown in Table 12 below.

TABLE 12

Effect On Subsequent Germination Of Placing Cells On Polyester Support Membranes Over Eradicants In Liquid Phase of Biphasic Embryo Development And Maturation Media Percentage Of Embryos Germinating After Development On Polyester Support Membranes

| Cell Line[1] | No liquid phase[2] | Liquid phase[3] | Liquid phase with 200 mg/L TIMENTIN ® Over Gelled Phase | Liquid phase with 400 mg/L TIMENTIN ® Over Gelled Phase |
|---|---|---|---|---|
| H1 | 92.5% | 95.0% | 72.5% | 95.0% |
| P1 | 42.5% | 55.0% | 35.0% | 17.5% |
| P2 | 62.5% | 67.5% | 52.5% | 47.5% |

[1]P1 = *P. taeda* cell line 1, P2 = *P. taeda* cell line 2, H1 = Hybrid pine cell line 1.
[2]Non-biphasic (gelled phase only, no liquid phase).
[3]Liquid phase without eradicants over gelled phase.

As shown in Table 12, and in similar results using AUGMENTIN® antibiotic or higher concentrations of TIMENTIN® antibiotic (500 and 800 mg/L), the application of a liquid phase between the gelled medium and the cells borne on a polyester support membrane, whether or not it contains eradicant, does not result in a significant detriment to embryo germination. Thus, if required due to long-term resurgence of bacterial growth in a culture, the method described in this example allows the application of antibiotics even in the presence of embryo development and maturation media in which they could not otherwise be effectively incorporated.

Example 4

Generation of Transformed Cells for Biphasic Selection Experiments, Using Particle Bombardment Transformation Loblolly and hybrid pine cell lines were used which had been grown and maintained as described in Examples 1–2 above. In order to test selection improvements that would be carried out alone or in combination with eradication procedures following *Agrobacterium* transformation, without confounding any growth effect related to the *Agrobacterium* gene transfer process and unrelated to the selection and eradication methods per se, transformed lines resistant to GENETICIN® were generated by the bombardment method described in U.S. patent application Ser. No. 09/318,136 filed on 25 May 1999, now U.S. Pat. No. 6,518,485, and New Zealand Patent No. 336149, each incorporated herein by reference.

Specifically, to prepare for gene transfer, a sterile fabric support (here NITEX, commercially available from Sefar Inc.) was placed in a sterile Buchner funnel and one to five milliliters of embryogenic suspension was pipetted onto the fabric support such that the embryogenic tissue was evenly distributed over the surface. The liquid medium was suctioned from the tissues using a mild vacuum. The fabric support with embryogenic tissue was removed from the Buchner funnel and placed on a GELRITE solidified $DCR_3$ preparation medium (Table 2) in 100×25 mm plastic petri dishes. Dishes were incubated in a dark growth chamber at 23° C.±2° C. for about 24–48 hours. The preparation medium of U.S. Pat. No. 6,518,485 contains 30 g maltose and 70 g PEG.

DNA was transferred into the tissues and/or embryos via carrier particle (microprojectile) bombardment technology using the PDS-1000/He BIOLISTICS® Particle Delivery System (available from Bio-Rad Laboratories). The DNAs of interest, here containing the visual marker gene uidA and the selection gene nptII, were precipitated onto the surface of gold microparticles, which were subsequently accelerated toward embryogenic tissue to penetrate the cell walls. Once inside the cells, DNA is released from the carrier particles and integrated randomly into the chromosomes.

The petri dishes with the fabric support and embryonic tissues were then placed into the interior of the PDS 1000/He BIOLISTICS® device and vacuum applied to a level of 28 inches Hg. The gold particles carrying the DNA were accelerated toward the embryogenic tissue following a helium build-up and bursting regulated by a 1550 psi rupture disk. In the PDS-1000/He BIOLISTICS® device the gap between the rupture disk and the macrocarrier (gap distance) was five mm and the macrocarrier travel distance was 13 mm. Following DNA transfer the petri dishes containing the fabric support and tissues were incubated in a dark growth chamber at 23° C.±2 C. for about 24 hours. The tissues and fabric support were transferred to semi-solid maintenance medium, $DCR_1$ (Table 2) to recover from carrier particle bombardment and incubated in a dark growth chamber at 23° C.±2° C. for a period of 0–7 days (the duration depended on observation of when cell division had resumed in the pine cells). The tissues and fabric support were transferred to a selection medium, semi-solid maintenance medium $DCR_1$ containing a level of selection agent inhibitory to the growth of non-transformed cells. In this and subsequent examples the selection agent used was GENETICIN® antibiotic at 15–30 mg/L. The plates were incubated in a dark growth chamber at 23° C.±2° C. for about six to twelve weeks with the fabric supports containing the tissues being transferred to the same fresh culture medium every 2–3 weeks.

Active growth on the selection medium occurred in a number of isolated sectors on some of the petri dishes. Such active growth in the presence of selection agent is an indication that the growing tissues have integrated the selection gene into their chromosomes and are stably transformed. These areas of active growth were treated as independent transformation events and are henceforth referred to as sublines. The transgenic embryogenic tissue was multiplied by transferring growing transgenic sectors to fresh semi-solid maintenance $DCR_2$ medium supplemented with selection agent, referred to hereinafter as $DCR_5$ selection medium, or semi-solid maintenance WV52 medium supplemented with selection agent, referred to hereinafter as WV5 selection medium. Dishes were incubated in a dark growth chamber at 23° C.±2° C. The actively growing transgenic embryogenic tissue was transferred to fresh semi-solid maintenance $DCR_5$ selection medium at 2–3 week intervals for a period of about six to twelve weeks depending on the rate of growth of the individual sublines of the transgenic embryogenic tissue.

Stable transformation was verified through a combination of growth on selection medium, assay for expression of the visual marker gene (an inserted gus gene, encoding a β-glucuronidase enzyme expressing in tissue culture cells, and detected by deep blue staining of cells from each of the transgenic lines upon exposure to a colorigenic glucuronidase enzyme substrate, "X-gluc", commercially available from Inalco, Inc.), according to techniques well known to those skilled in the art of plant transformation, and polymerase chain reaction (PCR) amplification of specific segments of the transgene DNA sequence. These techniques were carried out using techniques well known to those skilled in the art of molecular biology. The tissue was then cryopreserved.

Cells of five transgenic pine lines (lines from four different P. taeda families and one hybrid line), and the corresponding five non-transformed origin lines still held in cryopreservation, were then retrieved, proliferated, and placed in suspension as described in Example 1 above. Using the SCV as the basis of calculation, 1:9 mixtures of the transgenic cell line and the corresponding non-transgenic cell line were made, in order to simulate, in a controlled fashion, the situation following transformation in which the rare transformed cells must be selected from the abundant non-transformed cells.

The 1:9 mixtures were immediately plated on polyester, nylon, or filter paper supports or placed directly on the surface of gelled medium as described in Example 2, with five replicate plates for each treatment and cell line combination. The medium used was $DCR_2$ containing 15 mg/L GENETICIN® antibiotic, hereinafter referred to as $DCR_5$ selection medium, which should kill the non-transformed tissue while allowing growth of the transformed tissue. To verify the ability of the $DCR_5$ selection medium to kill the non-transformed tissue, non-transformed cells were plated alone on the $DCR_5$ selection medium using 5 replicate plates per line per treatment in the same support treatments of nylon, polyester, filter paper, and directly on the gelled medium. To verify the ability of the $DCR_5$ selection medium to allow growth of the transformed tissue, transformed cells were plated alone on the $DCR_5$ selection medium using 5 replicate plates per line per treatment in the same support treatments of nylon, polyester, filter paper, and directly on the gelled medium.

Cells, or the supports bearing the cells, were transferred onto fresh selection medium at biweekly intervals, and fresh weight of cells for each plate was recorded at each biweekly transfer, for a total of eight weeks (Table 13). Additionally, one plate per line by treatment combination was flooded with X-gluc at 4 weeks, and another at 8 weeks, for examination as to the proportion of cells that stained positive for GUS activity. These data allowed conclusions as to the efficacy of selection of cells submitted to each of the support membrane treatments. As a result of successful selection, growth of non-transgenic cells should be suppressed while growth of transgenic cells should be allowed. Thus it would be expected that plates bearing transgenic cells or a mixture of transgenic and non-transgenic cells would gain weight, while plates bearing only non-transgenic cells should show no weight gain. Furthermore, as a result of successful selection, plates that originally bore a mixture of non-transgenic and transgenic cells should be observed to have only cells staining positively for GUS cells rather than a random mixture of GUS-staining cells with cells that remain colorless upon exposure to X-gluc.

TABLE 13

Growth Of Non-transgenic, Transgenic, And 9:1 Mixed Pine
Cell Cultures On Selection Medium With Various Support Treatments

| Line or mixture[1] | Cells plated directly on medium | | Cells on filter paper support over medium | | Cells on nylon support membrane over medium | | Cells on polyester support membrane over medium | |
|---|---|---|---|---|---|---|---|---|
| | First 4 wk | All 8 wk | First 4 wk | All 8 wk | First 4 wk | All 8 wk | First 4 wk | All 8 wk |
| P1 | −0.054 ± 0.032 | −0.075 ± 0.010 | 0.204 ± 0.021 | 0.173 ± 0.054 | 0.006 ± 0.029 | 0.003 ± 0.029 | −0.026 ± 0.021 | −0.020 ± 0.024 |
| P1-T | 0.088 ± 0.068 | 4.835 ± 1.030 | 0.224 ± 0.056 | 4.458 ± 0.462 | −0.010 ± 0.022 | −0.020 ± 0.050 | 0.062 ± 0.037 | 3.420 ± 0.946 |
| 9:1 mixture P1:P1-T | −0.054 ± 0.015 | 0.163 ± 0.190 | 0.118 ± 0.013 | 0.225 ± 0.083 | −0.018 ± 0.018 | −0.013 ± 0.025 | 0.012 ± 0.026 | 0.055 ± 0.062 |
| P2 | −0.044 ± 0.018 | −0.060 ± 0.008 | 0.130 ± 0.016 | 0.057 ± 0.064 | 0.000 ± 0.024 | 0.005 ± 0.031 | 0.020 ± 0.010 | 0.007 ± 0.013 |
| P2-T | 3.798 ± 0.477 | 4.538 ± 0.549 | 3.838 ± 1.081 | 6.330 ± 1.508 | 0.150 ± 0.166 | 3.060 ± 1.320 | 5.672 ± 0.798 | 5.553 ± 0.680 |
| 9:1 mixture P2:P2-T | 0.460 ± 0.399 | 4.840 ± 1.523 | 0.316 ± 0.130 | 3.840 ± 1.008 | −0.002 ± 0.031 | 0.000 ± 0.024 | 0.192 ± 0.068 | 3.650 ± 1.603 |
| P3 | −0.047 ± 0.015 | −0.050 ± 0.014 | 0.178 ± 0.011 | 0.123 ± 0.059 | 0.002 ± 0.031 | 0.005 ± 0.026 | 0.008 ± 0.025 | −0.002 ± 0.017 |
| P3-T | 0.465 ± 0.093 | 1.500 ± 0.367 | 0.612 ± 0.248 | 2.513 ± 0.406 | 0.028 ± 0.058 | 0.120 ± 0.174 | 0.382 ± 0.138 | 1.615 ± 0.369 |
| 9:1 mixture P3:P3-T | 0.055 ± 0.079 | 1.103 ± 0.249 | 0.274 ± 0.081 | 1.100 ± 0.485 | 0.018 ± 0.023 | 0.050 ± 0.099 | 0.032 ± 0.040 | 0.365 ± 0.286 |
| P4 | −0.046 ± 0.009 | −0.060 ± 0.010 | 0.200 ± 0.117 | 0.135 ± 0.064 | −0.046 ± 0.036 | −0.120 ± 0.017 | −0.050 ± 0.035 | −0.073 ± 0.032 |
| P4-T | 1.662 ± 0.325 | 2.960 ± 0.765 | 4.472 ± 2.425 | 7.160 ± 1.857 | 0.342 ± 0.315 | 3.497 ± 1.325 | 2.656 ± 1.534 | 4.563 ± 0.617 |
| 9:1 mixture P4:P4-T | 0.444 ± 0.165 | 3.207 ± 0.206 | 1.754 ± 1.554 | 5.947 ± 0.821 | −0.006 ± 0.067 | 3.187 ± 0.451 | 1.532 ± 0.990 | 5.530 ± 0.718 |
| H1 | −0.034 ± 0.009 | −0.040 ± 0.017 | 0.268 ± 0.033 | 0.210 ± 0.072 | −0.032 ± 0.024 | −0.047 ± 0.029 | 0.092 ± 0.251 | −0.010 ± 0.017 |
| H1-T | 2.822 ± 0.388 | 3.283 ± 1.167 | 5.830 ± 0.900 | 4.957 ± 1.364 | 1.596 ± 0.935 | 3.947 ± 1.540 | 3.240 ± 1.940 | 8.867 ± 1.835 |
| 9:1 mixture H1:H1-T | 0.580 ± 0.144 | 5.313 ± 0.818 | 1.160 ± 0.321 | 9.453 ± 0.314 | 0.454 ± 0.754 | 4.670 ± 0.270 | 1.576 ± 1.267 | 6.703 ± 2.066 |

[1]P1 = *P. taeda* cell line 1, P1-T = *P. taeda* cell line 1, with inserted nptII and gus, P2 = *P. taeda* cell line 2, P2-T *P. taeda* cell line 2, with inserted nptII and gus, P3 = *P. taeda* cell line 3, P3-T = *P. taeda* cell line 3, with inserted nptII and gus, P4 = *P. taeda* cell line 4, P4-T = *P. taeda* cell line 4, with inserted nptII and gus, H1 = Hybrid pine cell line 1, H1-T = Hybrid pine cell line 1, with inserted nptII and gus.

As can be noted in Table 13, and as was also plainly observable in the GUS staining pattern, for all lines as measured at four weeks the filter paper support treatments allowed growth of non-transformed cells as well as transformed cells, clearly failing to "select" only transformed cells. Only following eight weeks of selection could four of the five transgenic lines be distinguished clearly within the mixed cultures on filter paper supports.

Growth of all cells was poor on the nylon support membrane treatments, so few transformed cells survived on the nylon support membranes. Only one transgenic line was growing detectably on the nylon support membranes at four weeks, while even at eight weeks only three of the five lines had been able to grow on the nylon membranes. As with the filter paper treatments, in the nylon support treatments the GUS staining pattern demonstrated that the growing cultures contained non-transformed, non-staining cells. Thus, the nylon support membrane treatments also resulted in capture of only 60% of the actual number of transformed cell lines from the mixtures, and the "captured" events remained chimaeric, containing multiple non-transformed "escape" cells. In conclusion, both the nylon and filter paper treatments, often used for selection of plant tissue cultures, required lengthier exposure to the selection medium in order to capture the majority of transformation events, allowed the growth of non-transformed cells within the mixture (which would regenerate "escapes"), and were unable to capture all transformation events.

Over the polyester support membranes, in contrast, three of the five transformed lines were distinguishable by growth at the end of four weeks, and the GUS staining patterns revealed that the growing cells were expressing GUS uniformly. At the end of eight weeks, all five of the transformant lines had been successfully selected from their non-transformed counterparts.

The treatment in which cells were plated directly on the selection medium, another often used method, showed good selection of transformed cells from non-transformed cells. At four weeks into selection, three of the five transgenic cell lines could be distinguished by growth exceeding that of non-transgenic cell lines, and at eight weeks into selection, all five transgenic lines could be distinguished. However, only in one of the five lines was the growth of the transgenic material plated directly on the selection medium comparable to that plated on the polyester support membranes. In conclusion, the polyester support membranes allowed as much effective penetration of the cells by the selection agent as did plating directly on the medium, but allowed better growth and proliferation of the transgenic material selected.

The results were that transformed pine cells, as evidenced by histochemical staining for the expression of a reporter gene, were able to grow to greater weights over polyester membranes than over nylon membranes, filter paper, or over gelled media without fabric supports. Furthermore, untransformed "escape" cells were not seen in as great a frequency over polyester membranes as over nylon membranes or over filter paper supports. This indicates that the efficiency of selection was significantly improved with the use of polyester supports.

Example 5

Eradication of Agrobacterium from Agrobacterium-Transformed Cells Concomitant with Selection of Transformants Lines transformed with Agrobacterium and washed as described in Example 1 above were plated onto gelled $DCR_5$ selection media as described in Example 4 above, and freed of any remaining Agrobacterium contamination using the biphasic eradicant treatments described in Example 3 above, specifically using the antibiotic combination TIMENTIN® antibiotic at 400–800 mg/L in a $DCR_4$ liquid medium poured over the gelled $DCR_5$ selection media. Lines were transferred onto fresh selection media at intervals of 2–3 weeks. When each transformed subline had grown to approximately 2 g, the presence of the transgenes was verified using polymerase chain reaction (PCR) amplification of specific segments of the transgene DNA sequence carried out using techniques well known to those skilled in the art of molecular biology. This demonstrated that the improved selection methods described in Example 4 above were sufficient to select transformed cells, without the number of escapes seen when the unimproved selection methods were used.

In addition, the absence of undetected Agrobacterium contamination was tested by PCR amplification of a sequence from an Agrobacterium virulence gene VirD. The VirD sequence was successfully amplified from positive controls and contaminated pine tissue in order to demonstrate its value as a control. This demonstrated that the eradication methods described in Examples 1 and 3 were sufficient to eradicate Agrobacterium while allowing normal growth and development of the embryogenic cells.

Embryos of normal appearance were developed and matured from the transgenic lines, which were then germinated as described in Example 2 above, and germinating embryos were transferred to MAGENTA® boxes containing 50–100 ml of $MSG_3$ medium for conversion to plantlets. Continued uidA expression was verified in samples from mature embryos and germinated plantlets. MAGENTA® boxes containing elongating plantlets were incubated in the light at 27°±3° C. for about eight to twelve weeks. Plantlets with white, healthy roots and an actively growing epicotyl were then transferred to a soil mix and placed under mist in a shaded greenhouse, then removed from mist, then moved to an outdoor shaded area, for acclimation before moving to full sun conditions. These treestocks were then planted on an operationally prepared site with 9 feet between rows. The trees were planted 6 feet apart along the center of the rows. Survival in the field site has been approximately 97%. Finally, the presence of the transgenes in the genomic DNA of the regenerated, field-planted pine transformants was demonstrated by continued expression of the uidA gene in both needle and woody tissue in the field samples through a change of seasons, as well as by Southern blotting of genomic DNA extracted from the needles of the field samples by techniques well known to those skilled in the art of plant transformation. To our knowledge, this is the first field planting of Agrobacterium-transformed pines derived from somatic embryogenic lines of hard pine species worldwide.

Example 6

Transformation and Regeneration of Pinus radiata

In this example the methods described for the transformation of the Southern yellow pine P. taeda and hybrids with the Eastern hard pine species P. rigida are extended to another hard pine species (i.e., a species of the genus Pinus, subgenus Pinus ), Pinus radiata, which is known to those skilled in the art of dendrology to be quite divergent from the preceding species, as demonstrated by the fact that even when it is grown sympatrically it does not readily hybridize with the preceding species. Accordingly, a skilled artisan would recognize that the teachings contained in the application is enabling for hard pine species (species of the genus Pinus subgenus Pinus ), and interspecies hybrids of the hard pines.

In this example, transformation, selection, and eradication experiments were conducted using somatic embryogenic cell lines from five different Pinus radiata families wherein a standard commonly-used somatic embryogenesis process was followed and, by making only the changes taught in the method described in this application in the preceding examples, transgenic Pinus radiata was produced. In the above examples, the media described in cited U.S. Patents as being sufficient to promote growth and embryogenesis of southern yellow pines and hybrids were adapted by our method to create media for the purposes of eradicating Agrobacterium and selecting transformants. In the present example, the maintenance media described in U.S. Pat. No. 5,565,355 (which is hereby incorporated by reference) as being sufficient to promote growth of P. radiata are adapted by our improved method to create preparation, recovery, selection, and eradication media for the purposes of transforming P. radiata somatic embryogenic cells with Agrobacterium, eradicating Agrobacterium and selecting transformants. These examples serve to illustrate that any nutrient media that have been established as sufficient to promote growth or embryogenesis of the target tissue may be employed in conjunction with the present method without undue experimentation. The maintenance medium of U.S. Pat. No. 5,565,355 is:

| Standard Embryogenesis Medium (embryogenic tissue maintenance medium): | |
|---|---|
| Major ion stock | 40 ml |
| Minor ion stock | 20 ml |
| Iron chelate stock | 20 ml |
| Vitamin stock | 10 ml |
| Inositol | 1.0 gm |
| Sucrose | 30.0 gm |
| Difco Bacto agar | 8.0 gm |
| (Adjust pH to 5.6–5.8 before addition of agar and autoclaving. Add filter sterilized amino acids after autoclaving.) | |

| Major Ion Stock (make up to 400 ml): | |
|---|---|
| Compound | Weight (gm) |
| $KNO_3$ | 14.31 |
| $MgSO_4.7H_2O$ | 4.00 |
| $CaCl_2.2H_2O$ | 0.25 |
| $NaNO_3$ | 3.10 |
| $NH_4H_2PO_4$ | 2.25 |

-continued

Minor Ion Stock (make up to 200 ml):

| Compound | Weight (mg) |
|---|---|
| $MnSO_4 \cdot 4H_2O$ | 36.0 |
| $H_3BO_3$ | 80.0 |
| $ZnSO_4 \cdot 7H_2O$ | 250.0 |
| KI | 10.0 |
| $CuSO_4 \cdot 5H_2O$ | 24.0 |
| $Na_2MoO_4 \cdot 2H_2O$ | 2.0 |
| $CoCl_2 6H_2O$ | 2.0 |

Iron Stock (make up to 1 liter):

| | |
|---|---|
| $FeSO_4 \cdot 7H_2O$ | 1.5 gm |
| $Na_2EDTA$ | 2.0 gm |

Vitamin Stock (make up to 1 liter):

| | |
|---|---|
| Thiamine HCl | 0.5 gm |
| Nicotinic Acid | 0.5 gm |
| Pyridoxine HCl | 0.05 gm |

Amino Acids:

| amino acid | amount |
|---|---|
| glutamine | 110 mg/L |
| asparagine | 105 mg/L |
| arginine | 35 mg/L |
| minor amino acids stock | 2 ml/L |

Minor Amino Acids Stock (make up to 800 ml):

| Amino Acid | weight (gm) |
|---|---|
| citrulline | 1.58 |
| ornithine | 1.52 |
| lysine | 1.10 |
| alanine | 0.8 |
| proline | 0.7 |

(Dispense into 40 ml aliquots. Freeze immediately, store frozen, and thaw only on day of use. Adjust pH to 5.6–5.8 and filter sterilize before use.)

In this example, immature seed cones were collected from several *P. radiata* sources located in breeding orchards in New Zealand. The seed cones were collected when the dominant zygotic embryo was at the precotyledonary stage of development. Using the classification system of von Arnold and Hakman (1988), the dominant zygotic embryo at this stage is referred to as being at stage 2; that is, an embryo with a prominent embryonic region with a smooth and glossy surface, subtended by elongated suspensor cells which are highly vacuolated. Megagametophytes containing developing zygotic embryos were used as the explant for culture initiation. The media and methods used to handle the cultures once they were initiated are those disclosed in U.S. Pat. No. 5,565,355. Once cultures were extruded, cryopreserved, and then retrieved, they were subjected to the procedures described in this example.

To test the growth of *Pinus radiata* cells over support membranes as described in Example 2 above or biphasic media as described in Example 3 above, cells of lines derived from five different *P. radiata* families were plated, as described in Example 2 above, on the following treatments:

A. Cells were placed directly onto maintenance medium with no support filter or membrane.

B. Cells were placed on a nylon support membrane (NITEX® fabric support with pre-wetting pore size 35, commercially available from SEFAR), and this membrane bearing the embryogenic cells was then placed on maintenance medium.

C. Cells were placed on a polyester support membrane (PECAP® fabric support with pre-wetting pore size 35, commercially available from SEFAR), and this membrane bearing the embryogenic cells was then placed on maintenance medium.

D. Cells were placed on a filter paper (WHATMAN® filter paper No. 3), which had been wetted with a few drops of liquid maintenance medium (the same as the gelled maintenance medium but lacking gelling agent), and this filter paper bearing the embryogenic cells was then placed on maintenance medium.

E. Cells were placed on a polyester support membrane (PECAP® fabric support with pre-wetting pore size 35, commercially available from SEFAR), and this membrane bearing the embryogenic cells was then placed over gelled maintenance medium on which had been placed a filter paper (WHATMAN® filter paper No.3) that had been wetted with a few drops of liquid maintenance medium (the same as the gelled maintenance medium but lacking gelling agent).

F. Cells were placed on a polyester support membrane (PECAP® fabric support with pre-wetting pore size 35, commercially available from SEFAR®), and this membrane bearing the embryogenic cells was then placed over gelled maintenance medium on which had been placed a filter paper (WHATMAN® filter paper No.3) that had been wetted with a full milliliter of liquid maintenance medium (the same as the gelled maintenance medium but lacking gelling agent).

The cells on their supports were weighed (cells in treatment A were weighed on a polyester support membrane and then gently scraped off the membrane using sterile forceps, or a sterile plastic one-use cell harvester, onto the gelled media) and were then maintained on the same supports, with weighing and transfer to fresh sterile gelled medium biweekly for four transfer cycles.

TABLE 14

Growth Of *Pinus radiata* Cell Cultures During 6 Weeks On Various Support and BiphasicTreatments

| *P. radiata* Embryogenic Cell Line | Average (n = 3) difference between weights (in grams) at start and end of 6 weeks | | | | | |
|---|---|---|---|---|---|---|
| | Treatment A | Treatment B | Treatment C | Treatment D | Treatment E | Treatment F |
| from family F | 1.02 ± 0.08 | 1.85 ± 0.38 | 2.77 ± 0.58 | 2.43 ± 0.30 | 3.46 ± 1.72 | 2.34 ± 0.12 |
| from family X | 1.47 ± 0.31 | 2.28 ± 0.14 | 3.48 ± 0.50 | 3.90 ± 0.25 | 4.35 ± 0.74 | 3.08 ± 0.68 |
| from family K | 1.21 ± 0.07 | 2.00 ± 0.70 | 3.09 ± 0.36 | 2.31 ± 0.26 | 1.53 ± 0.65 | 1.22 ± 0.78 |

TABLE 14-continued

Growth Of *Pinus radiata* Cell Cultures During
6 Weeks On Various Support and BiphasicTreatments

| *P. radiata* Embryogenic | Average (n = 3) difference between weights (in grams) at start and end of 6 weeks | | | | | |
|---|---|---|---|---|---|---|
| Cell Line | Treatment A | Treatment B | Treatment C | Treatment D | Treatment E | Treatment F |
| from family D | 1.35 ± 0.03 | 3.31 ± 0.33 | 3.70 ± 0.60 | 2.31 ± 0.57 | 2.52 ± 1.38 | 1.68 ± 0.48 |
| from family Q | 0.40 ± 0.04 | 1.00 ± 0.23 | 1.75 ± 0.30 | 1.01 ± 0.22 | 0.87 ± 0.32 | 0.50 ± 0.34 |

As can be seen in Table 14, for no cell line was the average growth over a period of six weeks less for cells grown over support membranes and biphasic treatments than for cells grown directly on gelled medium. Because the membrane supports facilitate rapid transfer and weighing with minimal manipulation of the cells, damage that cells sustain during transfer between gelled media without membrane supports, as described in Example 2 above, may account for some of the difference between Treatment A and the other treatments. Also, for all *P. radiata* cell lines, as had been shown for *P. taeda* and *P. rigida* hybrids in Example 2 above, growth on a polyester membrane support was superior to growth on a nylon membrane support or a filter paper support alone. The same patterns were observed in data analyzed for a single two-week transfer period. Embryos were subsequently successfully developed, matured, and germinated from *P. radiata* cells of these lines that had been maintained on polyester support membranes. These data suggested that polyester membrane supports could be used to facilitate washing, eradication and selection following *Agrobacterium* transformation of *P. radiata* as they had been used for *P. taeda* and *P. rigida* hybrids in the methods described in Examples 3, 4 and 5 above. This also illustrates that the present invention is not limited to any single basal culture nutrient medium formulation. It should be understood that any nutrient media commonly used in *Pinus* somatic embryogenesis will be suitable for use with this method.

Prior to gene transfer, tissue cultures were resuspended in $DCR_4$ liquid maintenance medium (Table 2) for pipetting onto a sterile fabric support placed in a sterile Buchner funnel. One to five milliliters of embryogenic suspension was pipetted onto the fabric support such that the embryogenic tissue was evenly distributed over the surface, after which the liquid medium was suctioned from the tissues using a mild vacuum. The sterile fabric support bearing *P. radiata* embryogenic tissue was placed on a preparation medium in 100×25 mm plastic petri dishes. In the method of our invention, preparation media are based on nutrient media sufficient to promote growth of the target tissue. Any nutrient media that have been established as sufficient to promote growth of the target tissue may be modified to prepare the cells for transformation. In this example, the preparation medium consisted of the basal medium described in U.S. Pat. No. 5,565,355 modified by levels of the plant growth regulator BAP varied from 0.6 to 6 mg/l, the substitution of 60.0 g/l of either maltose or sucrose, and the addition of 70.0 g/l of polyethylene glycol, and solidified with 3.25 g/l gellan gum.

Dishes were incubated in a dark growth chamber at 23° C.±2° C. for 24 hours prior to inoculation with *Agrobacterium* strain EHA105 transformed with a binary plasmid encoding uidA and nptII in the T-DNA, and induced for virulence by standard methods well known to those skilled in the art. Those skilled in the art will further recognize that the method is applicable for a variety of different inoculation and co-cultivation methods, strains and plasmids. Following inoculation the cells were incubated in a dark growth chamber at 23° C.±2° C. for about 72 hours.

Following this co-cultivation period, cells were washed according to the method described in Example 1, using polyester support membranes, wide-mouthed "baby food" jars with aerated lids, and wash medium identical to the maintenance medium except that gelling agents were omitted and 400 mg/l TIMENTIN® antibiotic was added. The cells were washed three times, with the first washes lasting 1–2 hours and the third wash being an overnight agitation in wash medium at approximately 100 rpm.

The tissues and fabric support were then transferred to semi-solid maintenance medium for one week in order to observe whether *Agrobacterium* contamination resurged, followed by transfer to selection medium. Selection media consist of nutrient media modified such that they allow preferential growth of transformed cells. For the purposes of this example, maintenance medium identical to the aforementioned medium, except for the addition of 400 mg/l TIMENTIN® antibiotic and 15 mg/l GENETICIN® antibiotic selection agent, which was shown to be inhibitory to the growth of non-transformed *P. radiata* cells, is referred to as *P. radiata* selection medium. The plates were incubated in a dark growth chamber at 23° C.±2° C. for about six weeks with the fabric supports containing the tissues being transferred to the same fresh culture medium every two weeks.

Active growth on the selection medium occurred in a number of isolated sectors on some of the petri dishes. Such active growth in the presence of selection agent is an indication that the growing tissues have integrated the selection gene into their chromosomes and are stably transformed. These areas of active growth were treated as independent transformation events and are henceforth referred to as sublines. The transgenic embryogenic tissue was multiplied for another six weeks by transferring growing transgenic sectors to fresh semi-solid maintenance medium every two weeks. Dishes were incubated in a dark growth chamber at 23° C.±2° C.

Cells from actively growing sublines from selection medium, and cells growing on maintenance medium without selection, were also examined using stereomicroscopes for the expression of the visual marker gene uidA at 6 and 12 weeks after infection. All of the sublines capable of active growth on selection medium were seen to express levels of the visual marker gene product that enabled them to be readily distinguished from non-selected cells. Selection of stably transformed *P. radiata* sublines and successful eradication of the *Agrobacterium* by the improved selection and eradication processes described, as indicated by growth on the selection medium, expression of the visual marker gene product, and the absence of undetected contaminating *Agrobacterium*, was further confirmed by PCR amplification using primers designed to amplify sequences from an endogenous control and the uidA, nptII, and virD genes as described in Example 5. The results were that axenic transformants were recovered from four of the five *P. radiata* lines on which transformation had been attempted. In a subsequent experiment, stable axenic *Agrobacterium* transformants were also recovered from the fifth line and two additional lines.

Ten transformant *P. radiata* lines were subsequently placed on an embryo maturation medium suitable for *P. radiata* as described in U.S. Pat. No. 5,565,355, and transgenic cotyledonary embryos were successfully harvested and germinated from nine of the ten lines in order to give rise to transgenic plants, demonstrating that the improved processes successful in selection and eradication were not detrimental to regeneration of transformed *P. radiata* plants.

Example 7

Use of ABA in Selection Media with Transformed Tissue

Loblolly pine cell lines were used which had been grown and maintained as described in Example 1 above, and prepared for biolistic transformation as described in Example 4 above. Following bombardment the support membranes bearing the bombarded embryogenic cells were transferred to $DCR_2$ maintenance media for one week. Following this the support membranes bearing the bombarded embryogenic cells were divided among plates containing gelled DCR selection medium either with or without the addition of 10 mg/l abscisic acid (ABA), and cultured for three weeks. Cells selected on either type of selection medium during this first selection period on selection medium containing ABA were then divided among plates with and without ABA and cultured for a further three weeks. The same occurred in the next transfer, resulting in groups of cells that had been selected entirely in the absence of ABA, entirely in the presence of ABA, or in the presence of ABA for one of the three three-week selection periods. After the nine weeks of selection, the plates were examined for sublines growing in the presence of the GENETICIN® antibiotic selection agent, and cells from these sublines were observed for staining indicating the presence of the uidA transgene. The cells were also checked for the presence of sequences by PCR amplification using primers specific for both the uidA and nptII transgenes, and subsequently these results were further confirmed by Southern blotting, all techniques well known to those skilled in the art of plant transformation.

The results were that multiple transformants were obtained from each of the cell lines tested, but the number of transformants obtained from the treatment in which ABA was present during the entire period of transfer was equal to or greater than the number obtained for any other treatment for all lines tested.

Furthermore, transformants from a cell line of an elite family, progeny of the *P. taeda* elite line 7–56, were observed only on treatments that had contained ABA in the selection medium. In previous experiments without ABA present in the selection medium, no transformants had been detected following selection in any of twelve lines tested from the same family, or another family derived from the reciprocal cross. As shown by the present example, solely in treatments containing ABA in the selection media were we able to detect the first sublines from any line of this cross that survived selection and produced confirmed transformants. This result demonstrated that the previous failure to detect stable transformants from this family did not result from failure to transform any cells, but from failure of these transformed pine cells to grow during selection without ABA. Stable transformants were detected after nine weeks of selection in a treatment in which 10 mg/L ABA had been added to the medium only during the first three weeks of selection, and more transformants were detected in treatments in which ABA was added to the selection medium throughout the entire nine-week selection period. This result implies that the protective effect of the ABA which allows transformed cells to survive selection is already being exerted in the initial period of selection, but that it is beneficial throughout the selection period and that without it transformants are being lost before they can be detected.

Embryos were developed, matured, and germinated from some of these transformants by the methods described in Example 2. These germinants were grown into planting stock that has subsequently been planted into a field test by the methods described in Example 6. Survival in the field has been approximately 93%.

Example 8

Use of ABA in Culture Media During and After Transformation with *Agrobacterium*

Seven loblolly pine cell lines or hybrid cell lines from seven widely diverse genetic backgrounds were used which had been grown, maintained, and transformed using *Agrobacterium* as described in Example 1 above except that the preparation medium, used for preparation and co-cultivation of the cells, either contained or lacked ABA. Following eradication using wash medium as described in Example 5 above, polyester support membranes bearing approximately 0.1 g of embryogenic tissue were divided onto recovery media either containing or lacking ABA. Following a one-week recovery period during which the cells were observed for resurgence of *Agrobacterium*, the polyester support membranes bearing the pine somatic embryogenic tissue were divided onto DCR selection media either containing or lacking ABA. Concentrations of ABA used in all these media were 0, 10, and 30 mg/L.

Cells were maintained on the selection media, with transfer of the polyester support membranes to fresh selection media of the same composition, every two weeks for a total of eight weeks of selection. At the conclusion of this selection period, the plates were examined for sublines growing in the presence of the GENETICIN® selection agent, and cells from these sublines were observed for staining indicating the presence of the uidA transgene. The cells were also checked for the presence of sequences by PCR amplification using primers specific for both the uidA and nptII transgenes, techniques well known to those skilled in the art of plant transformation. The results are presented in Table 15.

TABLE 15

Effect of ABA Concentration on Average (n = 12) Number of Transformants observed per Selection Plate Bearing 0.1 g Agrobacterium-inoculated Pine Cells at Start of Recovery Concentration of ABA (mg/l) in P. taeda (P) or P. rigida Hybrid (H) Embryogenic Cell Line

| preparation medium | recovery medium | selection medium | H1 | P1 | P2 | P3 | P4 | P5 | P6 |
|---|---|---|---|---|---|---|---|---|---|
| 0 | 0 | 0 | 9.6 ± 4.8 | 0.0 ± 0.0 | 1.3 ± 1.9 | 20.3 ± 2.2 | 33.4 ± 13.5 | 0.4 ± 0.9 | 1.3 ± 1.2 |
| 0 | 0 | 30 | 21.1 ± 6.5 | 0.0 ± 0.0 | 8.8 ± 4.8 | 22.3 ± 5.4 | 34.9 ± 9.7 | 5.5 ± 3.1 | 3.3 ± 2.8 |
| 0 | 10 | 10 | 19.0 ± 6.5 | 0.0 ± 0.0 | 1.0 ± 1.0 | 23.3 ± 2.8 | 28.8 ± 11.6 | 2.4 ± 2.0 | 3.2 ± 1.4 |
| 0 | 10 | 30 | 21.6 ± 8.6 | 0.1 ± 0.3 | 0.3 ± 0.5 | 26.0 ± 6.9 | 30.9 ± 9.3 | 7.2 ± 2.1 | 3.2 ± 1.5 |
| 0 | 30 | 30 | 15.1 ± 4.9 | 0.8 ± 0.6 | 5.2 ± 6.1 | 18.6 ± 5.1 | 28.6 ± 7.6 | 3.3 ± 2.1 | 2.3 ± 2.6 |
| 10 | 10 | 10 | 21.9 ± 8.4 | 1.3 ± 0.9 | 10.0 ± 3.7 | 22.6 ± 4.3 | 27.8 ± 9.0 | 10.3 ± 2.4 | 4.5 ± 1.3 |
| 30 | 30 | 30 | 21.8 ± 9.9 | 0.4 ± 0.8 | 5.3 ± 2.5 | 21.1 ± 2.3 | 27.3 ± 7.4 | 14.3 ± 3.5 | 2.3 ± 1.1 |
| 30 | 10 | 10 | 22.9 ± 10.1 | 0.3 ± 0.5 | 5.9 ± 2.4 | 21.6 ± 3.6 | 22.7 ± 7.0 | 11.3 ± 2.4 | 3.1 ± 2.3 |
| 0 | 0 | 10 | 27.0 ± 11.2 | 0.3 ± 0.9 | 5.8 ± 2.3 | 21.7 ± 3.6 | 27.5 ± 11.4 | 18.1 ± 4.0 | 3.9 ± 1.5 |

Cell lines used in this experiment varied from highly transformable to never previously transformed, in order to see the effect of ABA on a variety of types. As can be seen in the Table 15, 10 or 30 mg/L ABA concentration in the preparation medium was neutral or beneficial to the observation of transformants. ABA in the recovery medium was similarly neutral or beneficial, except that it was required in both the recovery and selection medium in order to observe transformants in one line. ABA in the selection medium is clearly beneficial for several of the lines.

As shown in this example, pine somatic embryogenic masses of all lines cultured in the presence of either 10 or 30 mg/L ABA during and after co-cultivation with *Agrobacterium* showed fewer necrotic foci (these appeared upon microscopic examination to be derived from the death of precociously developing embryos in the cultures) than did pine somatic embryogenic masses which were cultured during and after co-cultivation on media that did not contain ABA.

In this example, transformants were obtained from all lines, including lines from two families that had never previously been transformed. In subsequent experiments using *Agrobacterium* transformation and the methods of this Example, transformants have been recovered in lines from every one of 12 families attempted, in an average of 71% of the lines attempted from any given family.

Multiple separate transformants of three *P. taeda* lines and a hybrid line generated in this example were cryopreserved and then retrieved, simultaneously with cells of the respective non-transformed origin lines retrieved from cryopreservation by the same operators and method, for testing of the effects of the transformation, recovery, eradication, and selection processes on their embryogenicity. Cells from two of these same lines that had been transformed by the bombardment method described in Example 8 above were also simultaneously retrieved and tested. The results were that cells retrieved from the cryopreserved bombardment-transformed lines had lower production of harvestable cotyledonary embryos than cells retrieved from the corresponding *Agrobacterium*-transformed sublines, and cells from the *Agrobacterium*-transformed sublines had, in some cases, lower average production of harvestable cotyledonary embryos than cells retrieved from the corresponding non-transformed origin lines, but *Agrobacterium*-transformed sublines from all the embryogenic lines tested were able to regenerate sufficient harvestable cotyledonary embryos for the production of planting stock using the methods described in Example 6. In the present Example transgenic embryos were found not to differ significantly from non-transgenic embryos in their ability to germinate and produce elongated epicotyls.

Transformants generated in this example, and numerous subsequent experiments using the methods of this example with cell lines initiated and maintained in various methods and using various *Agrobacterium* strains and plasmids, have been cryopreserved. Those skilled in the art will recognize that this illustrates that the methods used are applicable to recovering regenerable transformants from cell lines with a variety of histories and using a variety of methods and plasmids for transformation. Hundreds of embryos have now been developed, matured, and germinated from *Agrobacterium* transformants of both *P. taeda* and hybrid lines selected using the methods in this example. Using the methods described in Example 6, these embryos have been converted to treestocks suitable for field planting.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

BIBLIOGRAPHY

Becwar, M. R. et al. (1990). Initiation Of Embryogenic Cultures And Somatic Embryo Development In Loblolly Pine (*Pinus Taeda*). Canadian Journal of Forest Research 20:810–817.

Becwar, M. R. et al. (1995). Method for regeneration of coniferous plants by somatic embryogenesis. U.S. Pat. No. 5,413,930.

Becwar, M. R. et al. (1996). Method for regeneration of coniferous plants by somatic embryogenesis. U.S. Pat. No. 5,506,136.

Cello, L. M. and Olsen, W. L. (1984). Method for transforming plant cells. U.S. Pat. No. 4,459,355.

Coke, J. E. (1996). Basal nutrient medium for in vitro cultures of loblolly pine. U.S. Pat. No. 5,534,433.

Connett, M. B. et al. (1993). Toward Transformation of *Pinus radiata* Tissue that is Regenerable via Organogenesis. Third Queenstown Molecular Biology Meeting.

Fillatti, J. J. and Thomas, B. R. (1996). Transformation and foreign gene expression with plant species. U.S. Pat. No. 5,565,347.

Gupta, P. K. and Durzan, D. J. (1985). Shoot multiplication from mature trees of Douglas-fir (*Pseudotsuga menziesii*) and sugar pine (*Pinus lambertiana*). *Plant Cell Reports* 4:177–179.

Handley, L. W. III. (1999). Method for regeneration of coniferous plants by somatic embryogenesis in culture media containing abscisic acid. U.S. Pat. No. 5,856,191.

Handley, L. W. III and Godbey, A. P. (1996). Embryogenic Coniferous Liquid Suspension Cultures. U.S. Pat. No. 5,491,090.

Sederoff, R. R. et al. (1988). Method for transforming Pine. U.S. Pat. No. 4,886,937.

Séguin et al. (1999). Stable genetic transformation of white pine after cocultavation of embryogenic tissues with *Agrobacterium tumefaciens*, Abstract, Forest Biotechnology '99, Joint Meeting of The International Wood Biotechnology Symposium and IUFRO Working Party 2.04–06 Molecular Genetics of Trees, Oxford, UK, Jul. 11–16, 1999.

Smith, D. R. (1996). Growth Medium. U.S. Pat. No. 5,565,355.

Smith, R. H. et al. (1992). Method for transforming plants via the shoot apex. U.S. Pat. No. 5,164,310.

von Arnold and Hakman (1988). Regulation of somatic embryo development in Picea abies by abscisic acid (ABA). *Journal of Plant Physiology* 132:164–169.

Wenck, A. R. et al. (1999). High efficiency *Agrobacterium*-mediated transformation of Norway spruce and loblolly pine. *Plant Molecular Biology* 39:407–416.

What is claimed is:

1. A method for regenerating transgenic plants of pine of the genus *Pinus* subgenus *Pinus* which comprises:
   incubating pine cells of the *Pinus* subgenus with *Agrobacterium* for *Agrobacterium* transformation;
   minimizing damage to cells subsequent to *Agrobacterium* infection by washing cells with a liquid culture medium comprising inorganic nutrients, vitamins, amino acids, a carbohydrate source and an *Agrobacterium* eradicant, wherein said damage is physical damage to the cells and loss of the cells and wherein minimized damage is assessed by time period to regain pre-transformation growth rate;
   selecting transformed cells;
   culturing said transformed cells to produce transgenic somatic embryos; and
   germinating said transgenic somatic embryos to produce transgenic plants.

2. The method of claim 1, wherein said damage to cells is minimized by:
   (a) suspending cells having been incubated with *Agrobacterium* in the liquid culture medium;
   (b) agitating said liquid culture medium containing suspended cells to wash the cells and remove *Agrobacterium*; and
   (c) recovering washed cells with minimal damage.

3. The method of claim 2, wherein pine cells are plated onto a support membrane prior to *Agrobacterium* transformation.

4. The method of claim 1, wherein said damage to cells is minimized by:
   (a) plating pine cells having been incubated with *Agrobacterium* on a support membrane;
   (b) rinsing said cells using the liquid culture medium to remove *Agrobacterium*; and
   (c) recovering washed cells with minimal damage.

5. The method of claim 4, wherein pine cells are plated onto a support membrane prior to *Agrobacterium* transformation.

6. The method of claim 4, wherein pine cells are plated onto a support membrane subsequent to *Agrobacterium* transformation.

7. The method of claim 4, wherein steps (b) and (c) are repeated between 2 and 10 times.

8. The method of claim 4, wherein each wash is carried out for a duration sufficient to expose all the cells to the liquid culture medium, said wash carried out for between half an hour to overnight in duration.

9. The method of claim 4, wherein said support membrane is prepared from a material selected from the group consisting of polyester, polypropylene and a liquid permeable fluoropolymer fabric.

10. The method of claim 1, wherein said selection is performed by
    culturing washed cells with minimized damage on a support membrane placed over a gel medium;
    contacting said cells with a selection agent; and
    selecting transformed cells.

11. The method of claim 10, wherein said selection agent is contained in said gel medium.

12. The method of claim 10, wherein said selection agent is contained in a layer and said support membrane is placed over said layer which is placed on said gel medium.

13. The method of claim 12, wherein said layer is a layer of liquid medium.

14. The method of claim 12, wherein said layer is a layer of gelled medium.

15. The method of claim 12, wherein said layer is a filter paper with a liquid medium absorbed therein.

16. The method of claim 10, wherein said support membrane is prepared from a material selected from the group consisting of polyester, polypropylene and a liquid permeable fluoropolymer fabric.

17. The method of claim 11 which further comprises contacting the washed cells with an *Agrobacterium* eradicant.

18. The method of claim 17, wherein the eradicant is contained in a layer in or positioned over the gel medium containing the selection agent.

19. The method of claim 18, wherein said layer containing the eradicant is a layer of liquid medium.

20. The method of claim 18, wherein said layer containing the eradicant is a layer of gelled medium.

21. The method of claim 18, wherein said layer containing the eradicant is a filter paper with a liquid medium absorbed therein.

22. The method of claim 18, wherein said support membrane is prepared from a material selected from the group consisting of polyester, polypropylene and a liquid permeable fluoropolymer fabric.

23. A method for regenerating transgenic plants of pine of the genus *Pinus* subgenus *Pinus* which comprises:

incubating pine cells of the subgenus *Pinus* with *Agrobacterium* for *Agrobacterium* transformation;

minimizing damage to cells subsequent to *Agrobacterium* infection by washing cells with a liquid culture medium comprising inorganic nutrients, vitamins, amino acids, a carbohydrate source and an *Agrobacterium* eradicant, wherein said damage is physical damage to the cells and loss of the cells and wherein minimized damage is assessed by time period to regain pre-transformation growth rate;

selecting transformed cells by culturing washed cells with minimized damage on a support membrane placed over a gel medium, contacting said cells with a selection agent and selecting transformed cells;

culturing said transformed cells to produce transgenic somatic embryos; and germinating said transgenic somatic embryos to produce transgenic plants.

24. The method of claim 23, wherein said damage to cells is minimized by:
(a) suspending cells having been incubated with *Agrobacterium* in a liquid culture medium;
(b) agitating said liquid culture medium containing suspended cells to wash the cells and remove *Agrobacterium*; and
(c) recovering washed cells with minimal damage.

25. The method of claim 24, wherein pine cells are plated onto a support membrane prior to *Agrobacterium* transformation.

26. The method of claim 24 which further comprises contacting the washed cells with an *Agrobacterium* eradicant during selection.

27. The method of claim 26, wherein the eradicant is contained in a layer in or positioned over the gel medium containing the selection agent.

28. The method of claim 23, wherein said damage to cells is minimized by:
(a) plating pine cells having been incubated with *Agrobacterium* on a support membrane;
(b) rinsing said cells using the liquid culture medium to remove *Agrobacterium*; and
(c) recovering washed cells with minimal damage.

29. The method of claim 28, wherein pine cells are plated onto a support membrane prior to *Agrobacterium* transformation.

30. The method of claim 28, wherein pine cells are plated onto a support membrane subsequent to *Agrobacterium* transformation.

31. The method of claim 28 which further comprises contacting the washed cells with an *Agrobacterium* eradicant during selection.

32. The method of claim 31, wherein the eradicant is contained in a layer in or positioned over the gel medium containing the selection agent.

33. A method for minimizing damage to transformed cells of pine of the genus *Pinus* subgenus *Pinus* following infection by *Agrobacterium* for *Agrobacterium* transformation which comprises:
(a) washing transformed cells of the subgenus *Pinus* in a liquid culture medium comprising inorganic nutrients, vitamins, amino acids, a carbohydrate source and an *Agrobacterium* eradicant to minimize damage to the cells, wherein said damage is physical damage to the cells and loss of the cells and wherein minimized damage is assessed by time period to regain pre-transformation growth rate;
(b) plating said cells on a support membrane;
(c) suspending said cells in the liquid culture medium; and
(d) recovering washed cells with minimal physical damage.

34. The method of claim 33, wherein (i) cells are plated onto a support membrane and (ii) said cells are transformed prior to step (a).

35. The method of claim 33, wherein steps (b) and (c) are repeated between 2 and 10 times.

36. The method of claim 33 wherein each wash is carried out for a duration sufficient to expose all the cells to the liquid culture medium, said wash carried out for between half an hour to overnight in duration.

37. The method of claim 33, wherein said support membrane is prepared from a material selected from the group consisting of polyester, polypropylene and a liquid permeable fluoropolymer fabric.

38. The method of claim 3, wherein the support membrane containing the pine cells is placed over a gel medium for transformation, *Agrobacterium* is added to the pine cells on the support membrane and the pine cells and *Agrobacterium* are co-cultivated to produce transformed pine cells.

39. The method of claim 38, wherein the gel medium for transformation comprises polyethylene glycol (PEG) and a carbohydrate source that is maltose.

40. The method of claim 39, wherein the gel medium for transformation comprises 6% maltose and 7% PEG.

41. The method of claim 5, wherein the support membrane containing the pine cells is placed over a gel medium for transformation, *Agrobacterium* is added to the pine cells on the support membrane and the pine cells and *Agrobacterium* are co-cultivated to produce transformed pine cells.

42. The method of claim 41, wherein the gel medium for transformation comprises polyethylene glycol (PEG) and a carbohydrate source that is maltose.

43. The method of claim 42, wherein the gel medium for transformation comprises 6% maltose and 7% PEG.

44. The method of claim 25, wherein the support membrane containing the pine cells is placed over a gel medium for transformation, *Agrobacterium* is added to the pine cells on the support membrane and the pine cells and *Agrobacterium* are co-cultivated to produce transformed pine cells.

45. The method of claim 44, wherein the gel medium for transformation comprises polyethylene glycol (PEG) and a carbohydrate source that is maltose.

46. The method of claim 45, wherein the gel medium for transformation comprises 6% maltose and 7% PEG.

47. The method of claim 29, wherein the support membrane containing the pine cells is placed over a gel medium for transformation, *Agrobacterium* is added to the pine cells on the support membrane and the pine cells and *Agrobacterium* are co-cultivated to produce transformed pine cells.

48. The method of claim 47, wherein the gel medium for transformation comprises polyethylene glycol (PEG) and a carbohydrate source that is maltose.

49. The method of claim 48, wherein the gel medium for transformation comprises 6% maltose and 7% PEG.

50. The method of claim 11, wherein the gel medium for selection further comprises abscisic acid (ABA).

51. The method of claim 12, wherein the layer for selection further comprises abscisic acid (ABA).

52. The method of claim 23, wherein said selection agent is contained in said gel medium.

53. The method of claim 23, wherein said selection agent is contained in a layer and said support membrane is placed over said layer which is placed on said gel medium.

54. The method of claim 53, wherein said layer is a layer of liquid medium.

55. The method of claim 53, wherein said layer is a layer of gelled medium.

56. The method of claim 53, wherein said layer is a filter paper with a liquid medium absorbed therein.

57. The method of claim 52, wherein the gel medium for selection further comprises abscisic acid (ABA).

58. The method of claim 53, wherein the layer for selection further comprises abscisic acid (ABA).

59. A method for regenerating transgenic plants of pine of the genus *Pinus* subgenus *Pinus* which comprises:

transforming pine cells of the subgenus *Pinus* with *Agrobacterium* by plating the pine cells on a support membrane, placing the support membrane containing the pine cells over a gel medium for transformation, adding *Agrobacterium* to the pine cells on the support membrane and co-cultivating the pine cells and *Agrobacterium* to produce transformed pine cells;

minimizing damage to transformed pine cells subsequent to *Agrobacterium* transformation by washing cells with a liquid culture medium comprising inorganic nutrients, vitamins, amino acids, a carbohydrate source and an *Agrobacterium* eradicant, wherein said damage is physical damage to the cells and loss of the cells and wherein minimized damage is assessed by time period to regain pre-transformation growth rate;

selecting transformed cells by plating washed transformed cells with minimized damage on a support membrane, placing the support membrane containing the washed transformed pine cells over a gel medium, contacting the cells with a selection agent and selecting transformed cells;

culturing the selected transformed cells to produce transgenic somatic embryos; and germinating the transgenic somatic embryos to produce transgenic plants.

60. The method of claim 59, wherein the damage to cells is minimized by:
    (a) suspending the transformed cells in the liquid culture medium;
    (b) agitating the liquid culture medium containing suspended cells to wash the cells and remove *Agrobacterium*; and
    (c) recovering washed cells with minimal damage.

61. The method of claim 59, wherein the damage to cells is minimized by:
    (a) rinsing the transformed cells using the liquid culture medium to remove *Agrobacterium*; and
    (b) recovering washed cells with minimal damage.

62. The method of claim 61, wherein steps (a) and (b) are repeated between 2 and 10 times.

63. The method of claim 61, wherein each wash is carried out for a duration sufficient to expose all the cells to the liquid culture medium, the wash carried out for between half an hour to overnight in duration.

64. The method of claim 59, wherein the support membrane is prepared from a material selected from the group consisting of polyester, polypropylene and a liquid permeable fluoropolymer fabric.

65. The method of claim 59, wherein the selection agent is contained in the gel medium for selection.

66. The method of claim 59, wherein the selection agent is contained in a layer and the support membrane is placed over the layer which is placed on the gel medium for selection.

67. The method of claim 65, wherein the layer is a layer of liquid medium.

68. The method of claim 65, wherein the layer is a layer of gel medium.

69. The method of claim 65, wherein the layer is a filter paper with a liquid medium absorbed therein.

70. The method of claim 59 which further comprises contacting the washed cells with an *Agrobacterium* eradicant during selection.

71. The method of claim 70, wherein the eradicant is contained in a layer in or positioned over the gel medium containing the selection agent.

72. The method of claim 59, wherein the gel medium for transformation comprises polyethylene glycol (PEG) and a carbohydrate source that is maltose.

73. The method of claim 72, wherein the gel medium for transformation comprises 6% maltose and 7% PEG.

74. The method of claim 65, wherein the gel medium for selection further comprises abscisic acid (ABA).

75. The method of claim 66, wherein the layer for selection further comprises abscisic acid (ABA).

* * * * *